United States Patent [19]

Miki

[11] Patent Number: 5,505,696
[45] Date of Patent: Apr. 9, 1996

[54] TRANSFUSION DEVICE

[75] Inventor: Shigeichirou Miki, Yomatokoriyama, Japan

[73] Assignee: Sharp Kabushiki Kaisha, Osaka, Japan

[21] Appl. No.: 165,801

[22] Filed: Dec. 13, 1993

[30] Foreign Application Priority Data

Dec. 14, 1992 [JP] Japan ..................... 4-332922

[51] Int. Cl.$^6$ .................................. A61M 5/20
[52] U.S. Cl. ............................................ 604/67
[58] Field of Search ................. 604/246, 65, 30, 604/31, 48, 50, 53, 66, 67, 246, 250–256; 128/DIG. 13

[56] References Cited

U.S. PATENT DOCUMENTS 5,328,460  7/1994  Lord et al. ............... 128/DIG. 13

FOREIGN PATENT DOCUMENTS 217075   1/1990  Japan .
5168708  7/1993  Japan .
5277180  10/1993 Japan .

*Primary Examiner*—C. Fred Rosenbaum
*Assistant Examiner*—Manuel Mendez

[57] ABSTRACT

A transfusion device in which a transfusion tube is squeezed by a transfusion pump mechanism so as to feed transfusion solution in the transfusion tube through pressurization, comprising: a first member for setting size of air bubbles to be detected in the transfusion solution, which includes a bubble sensor; a second member for setting a transfusion rate and a transfusion quantity of the transfusion solution; a third member for calculating a pressurization feed rate of the transfusion solution on the basis of the transfusion rate and a cross-sectional area of the transfusion tube; a fourth member for calculating a permissible quantity of the air bubbles mixed into a unit volume of the transfusion solution on the basis of the size of the air bubbles and the transfusion rate; a fifth member for calculating an integrated value of the air bubbles per unit volume of the transfusion solution on the basis of the pressurization feed rate of the transfusion solution and output level of the bubble sensor; a sixth member for judging whether or not the integrated value of the air bubbles per unit volume of the transfusion solution exceeds the permissible quantity of the air bubbles mixed into the unit volume of the transfusion solution; and a seventh member for stopping, when the sixth member has formed an affirmative judgement, the transfusion pump mechanism.

4 Claims, 19 Drawing Sheets

Fig.5

AIR SIZE:INPUT
S.        M.        L.
1 2 3 4 5 6 7 8

*Fig.18*

```
CODE=  123456
RATE=  100-1500
VTBI=    0- 600
TIME=00:00-99:99
NET  = 650
```

*Fig.19*

| N | RATE | VTBI | |
|---|------|------|---|
| 1 | 125 | 500 | AB |

*Fig.20*

| N | RATE | VTBI | |
|---|------|------|---|
| 1 | 125 | 500 | ▓▓ |
| 2 | 60 | 100 | ▓▓▓ |
| 3 | 125 | 500 | ABE |

Fig.21

| N | RATE | VTBI | |
|---|------|------|---|
| 1 | 125  | 500  | ML |

Fig.22

| N | RATE | VTBI | |
|---|------|------|---|
| 1 | 125  | 500  | ML |
| 2 | 60   | 100  | ML |
| 3 | 125  | 500  | ML |

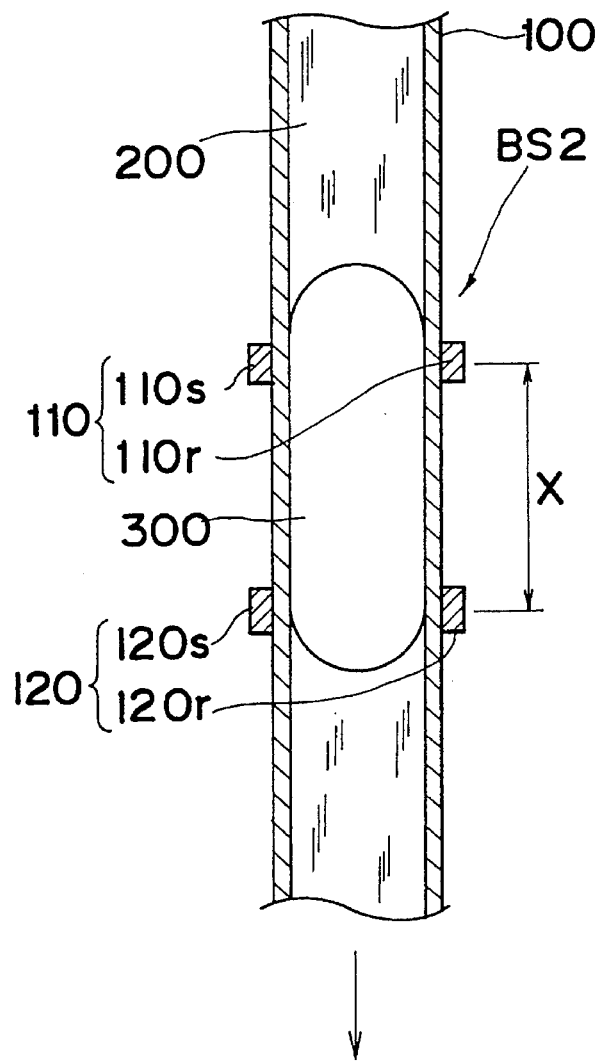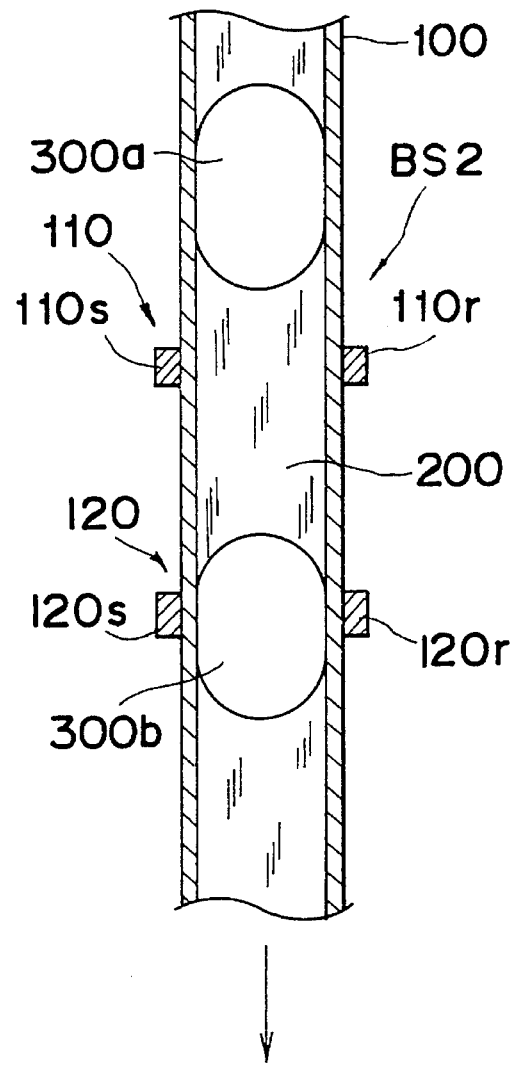
Fig. 23(a) PRIOR ART
Fig. 23(b) PRIOR ART

TRANSFUSION DEVICE

BACKGROUND OF THE INVENTION

The present invention relates to a transfusion device for feeding, by selecting a drug and designating quantity and rate of transfusion, its transfusion solution through pressurization, which is used as an intravenous infusion device or the like for drip.

Generally, in a known transfusion device, an intermediate portion of a transfusion tube having one end coupled with a drug solution bag and the other end coupled with an injection needle is set and transfusion solution (drug solution) in the transfusion tube is fed through pressurization by driving, for example, a linear peristaltic pump so as to be infused into a body of a patient.

Meanwhile, it is not desirable that air is mixed into drug solution infused into the body of the patient. When size of air bubbles in the drug solution is minute or quantity of air bubbles in the drug solution is small, air bubbles in the drug solution are permissible to some extent. However, when size and quantity of air bubbles in the drug solution exceed predetermined values, undesirable influences are exerted upon the body and in some cases, risk of life of the patient is incurred.

Therefore, in the known transfusion device of this kind, a bubble sensor is generally provided such that a processing against a malfunction is performed when air bubbles are detected in the drug solution.

FIGS. 23(a) and 23(b) show a conventional bubble sensor BS2 in which a pair of ultrasonic sensors 110 and 120 are provided on an outer peripheral surface of a transfusion tube 100 so as to be spaced a predetermined distance X from each other in a direction of flow of transfusion solution. The first ultrasonic sensor 110 is constituted by an ultrasonic transmitter 110s and an ultrasonic receiver 110r and the ultrasonic transmitter 110s and the ultrasonic receiver 110r are brought into contact with the outer peripheral 10 surface of the transfusion tube 100 so as to confront each other in a radial direction of the transfusion tube 100. In the second ultrasonic sensor 120, an ultrasonic transmitter 120s and an ultrasonic receiver 120r are likewise provided on the outer peripheral surface of the transfusion tube 100 so as to confront each other in the radial direction of the transfusion tube 100.

When transfusion solution (drug solution) 200 flows through the transfusion tube 100 relative to an ultrasonic path connecting the ultrasonic transmitter and the ultrasonic receiver, ultrasonic wave is propagated sufficiently, so that reception level of the ultrasonic receiver is high and thus, output of the ultrasonic transmitter exceeds a predetermined level. However, when an air bubble 300 is mixed into the transfusion solution 200 in the transfusion tube 100 as shown in FIG. 23(a) and passes through the ultrasonic path, propagation rate of ultrasonic wave drops greatly, thereby resulting in extreme drop of output level of the ultrasonic receiver. Mix of the air bubble 300 into the transfusion solution 200 is judged by detecting this extreme drop of output level of the ultrasonic receiver. Thus, when outputs of both of the ultrasonic receivers 110r and 120r of the first and second ultrasonic sensors 110 and 120 have dropped to low levels, it is judged that the air bubble 300 having a size larger than the distance X between the ultrasonic sensors 110 and 120 has been detected. In this case, drive of the peristaltic pump is stopped and an alarm or a warning display is given.

Meanwhile, in the known transfusion device, transfusion has been performed by setting drug in the transfusion device in accordance with indications such as prescription prior to transfusion and manually inputting data on quantity, rate and period of transfusion, etc. In another prior art transfusion device, the transfusion device and a controller for the transfusion device are connected to each other by a communication circuit such as a telephone circuit such that commands on quantity, rate and period of transfusion, etc. are set via the communication circuit.

In the case of the above mentioned bubble sensor BS2 of the known transfusion device, size of the air bubble 300 to be detected by the bubble sensor BS2 is determined by the distance X between the ultrasonic sensors 110 and 120. However, since the distance X between the ultrasonic sensors 110 and 120 is specific to the bubble sensor BS2, a lower limit of size of air bubbles capable of being detected by the bubble sensor BS2 is fixed at a predetermined value. Therefore, size of air bubbles to be detected by the bubble sensor BS2 cannot be adjusted arbitrarily according to patients ranging from adults to children and thus, the bubble sensor BS2 should be replaced for each patient.

Furthermore, as shown in FIG. 23(b), in case air bubbles 300a and 300b are, when passing through the bubble sensor BS2, separated from each other but are, after passing through the bubble sensor BS2, united with each other to a size requiring stop of the pump and the warning display, outputs of the ultrasonic receivers 110r and 120r do not become low levels simultaneously when the air bubbles 300a and 300b pass through the bubble sensor BS2. Therefore, the bubble sensor BS2 is set to an undetected state and thus, there is a risk that the body of the patient is adversely affected by the air bubbles 300a and 300b. Meanwhile, in case a malfunction of the transfusion tube 100 occurs upstream of the bubble sensor BS2 and air bubbles are mixed into the transfusion solution gradually, the small air bubbles cannot be detected by the bubble sensor BS2 when an operator continues to perform transfusion for a long time without noticing the malfunction. Thus, as a result of transfusion performed for a long time, there is a risk that a more harmful influence is exerted on the body of the patient.

In addition, the known bubble sensor is large in size due to the need for the two sets of the ultrasonic sensors.

Meanwhile, in the prior art transfusion device, there is a risk that when drug is set in the transfusion device, a wrong drug may be selected due to an error of an operator. Furthermore, erroneous data on quantity, rate and period of transfusion may be manually inputted by the operator.

SUMMARY OF THE INVENTION

Accordingly, an essential object of the present invention is to provide, with a view to eliminating the disadvantages inherent in conventional transfusion devices, a transfusion device in which detection accuracy of air bubbles mixed into transfusion solution is raised such that safety of the transfusion device is increased.

Another important object of the present invention is to provide a transfusion device in which wrong selection of a drug and erroneous input of various data through manual operation of an operator are prevented.

In order to accomplish these objects of the present invention, a first transfusion device in which a transfusion tube is squeezed by a transfusion pump mechanism so as to feed transfusion solution in the transfusion tube through pressurization, according to the present invention comprises: a first means for setting size of air bubbles to be detected in the transfusion solution, which includes a bubble sensor formed by an ultrasonic transmitter and an ultrasonic receiver; the ultrasonic transmitter and the ultrasonic receiver being provided, in the course of the transfusion tube, on an outer periphery of the transfusion tube so as to confront each other through the transfusion tube; a second means for setting a transfusion rate and a transfusion quantity of the transfusion solution; a third means for calculating a pressurization feed rate of the transfusion solution on the basis of the transfusion rate and a cross-sectional area of the transfusion tube; a fourth means for calculating a permissible quantity of the air bubbles mixed into a unit volume of the transfusion solution on the basis of the size of the air bubbles and the transfusion rate; a fifth means for calculating an integrated value of the air bubbles per unit volume of the transfusion solution on the basis of the pressurization feed rate of the transfusion solution and output level of the bubble sensor; a sixth means for judging whether or not the integrated value of the air bubbles per unit volume of the transfusion solution exceeds the permissible quantity of the air bubbles mixed into the unit volume of the transfusion solution; and a seventh means for stopping, when the sixth means has judged that the integrated value of the air bubbles per unit volume of the transfusion solution exceeds the permissible quantity of the air bubbles mixed into the unit volume of the transfusion solution, the transfusion pump mechanism.

Meanwhile, a second transfusion device in which a transfusion tube is squeezed by a transfusion pump mechanism so as to feed transfusion solution in the transfusion tube through pressurization, according to the present invention comprises: a first means for setting size of air bubbles to be detected in the transfusion solution, which includes a bubble sensor formed by an ultrasonic transmitter and an ultrasonic receiver; the ultrasonic transmitter and the ultrasonic receiver being provided, in the course of the transfusion tube, on an outer periphery of the transfusion tube so as to confront each other through the transfusion tube; a second means for setting a transfusion rate and a transfusion quantity of the transfusion solution; a third means for calculating a pressurization feed rate of the transfusion solution on the basis of the transfusion rate and a cross-sectional area of the transfusion tube; a fourth means for calculating a permissible quantity of the air bubbles mixed into the transfusion solution during a unit time period on the basis of the size of the air bubbles and the transfusion rate; a fifth means for calculating an integrated value of the air bubbles at an interval of the unit time period on the basis of the pressurization feed rate of the transfusion solution and output level of the bubble sensor; a sixth means for judging whether or not the integrated value of the air bubbles at the interval of the unit time period exceeds the permissible quantity of the air bubbles mixed into the transfusion solution during the unit time period; and a seventh means for stopping, when the sixth means has judged that the integrated value of the air bubbles at the interval of the unit time period exceeds the permissible quantity of the air bubbles mixed into the transfusion solution during the unit time period, the transfusion pump mechanism.

Moreover, a third transfusion device in which a transfusion tube is squeezed by a transfusion pump mechanism so as to feed transfusion solution in the transfusion tube through pressurization and data on transfusion factors such as transfusion quantity, transfusion rate and transfusion period are recorded on a drug container, a prescription or the like, according to the present invention comprises: a data reader for reading the data on the transfusion factors such that the data read from the drug container, the prescription or the like by the data reader is stored.

Furthermore, a fourth transfusion device in which a transfusion tube is squeezed by a transfusion pump mechanism so as to feed transfusion solution in the transfusion tube through pressurization, while first data on transfusion factors such as transfusion quantity, transfusion rate and transfusion period and second data of threshold values of the transfusion factors are recorded on a drug container, a prescription or the like, according to the present invention comprises: a data reader for reading the first data and the second data; the first data and the second data being read from the drug container, the prescription or the like by the data reader so as to be stored such that a warning is issued when the transfusion factors have deviated from the threshold values of the transfusion factors.

In addition, a fifth transfusion device in which a transfusion tube is squeezed by a transfusion pump mechanism so as to feed transfusion solution in the transfusion tube through pressurization, while first and second drug codes for identifying kinds of drugs are, respectively, recorded on a drug container and a prescription or the like, according to the present invention comprises: a data reader for reading the first and second drug codes such that a warning is issued when it is found as a result of comparison between the first drug code read from the drug container by the data reader and the second drug code read from the prescription or the like by the data reader that the first drug code does not coincide with the second drug code.

In the first transfusion device, the size of the air bubbles to be detected, the transfusion rate and the transfusion quantity are set and the permissible quantity of the air bubbles mixed into the unit volume of the transfusion solution is calculated on the basis of the size of the air bubbles and the transfusion rate. Meanwhile, presence or absence of the air bubbles in the transfusion solution is detected by the bubble sensor and the integrated value of the air bubbles per unit volume of the transfusion solution is calculated on the basis of the output level of the ultrasonic receiver of the bubble sensor and the pressurization feed rate. Thus, when the integrated value of the air bubbles per unit volume of the transfusion solution exceeds the permissible quantity of the air bubbles mixed into the unit volume of the transfusion solution, pressurization feed of the transfusion solution is automatically stopped by stopping the transfusion pump mechanism.

Meanwhile, in the second transfusion device, the size of the air bubbles to be detected, the transfusion rate and the transfusion quantity are set and the permissible quantity of the air bubbles mixed into the transfusion solution during the unit time period is calculated on the basis of the size of the air bubbles and the transfusion rate. Meanwhile, presence or absence of the air bubbles in the transfusion solution is detected by the bubble sensor and the integrated value of the air bubbles at the interval of the unit time period is calculated on the basis of the output level of the ultrasonic receiver of the bubble sensor and the pressurization feed rate. Thus, when the integrated value of the air bubbles at the interval of the unit time period exceeds the permissible quantity of the air bubbles mixed into the transfusion solution during the unit time period, pressurization feed of the transfusion solution is automatically stopped by stopping the transfusion pump mechanism.

In the third transfusion device, the data on the transfusion factors such as the transfusion quantity, the transfusion rate and the transfusion quantity is inputted so as to be set.

Meanwhile, in the fourth transfusion device, when the transfusion factors such as the transfusion quantity, the transfusion rate and the transfusion period, which deviate from their threshold values, a warning is issued and thus, erroneous input of the transfusion factors is prevented.

Furthermore, in the fifth transfusion device, since the first drug code recorded on the drug container and the second drug code recorded on the prescription or the like are read so as to be compared with each other such that a warning is issued when the first and second drug codes do not coincide with each other, use of an erroneous drug is prevented.

BRIEF DESCRIPTION OF THE DRAWINGS

These objects and features of the present invention will become apparent from the following description taken in conjunction with the preferred embodiments thereof with reference to the accompanying drawings, in which:

Figure 5:
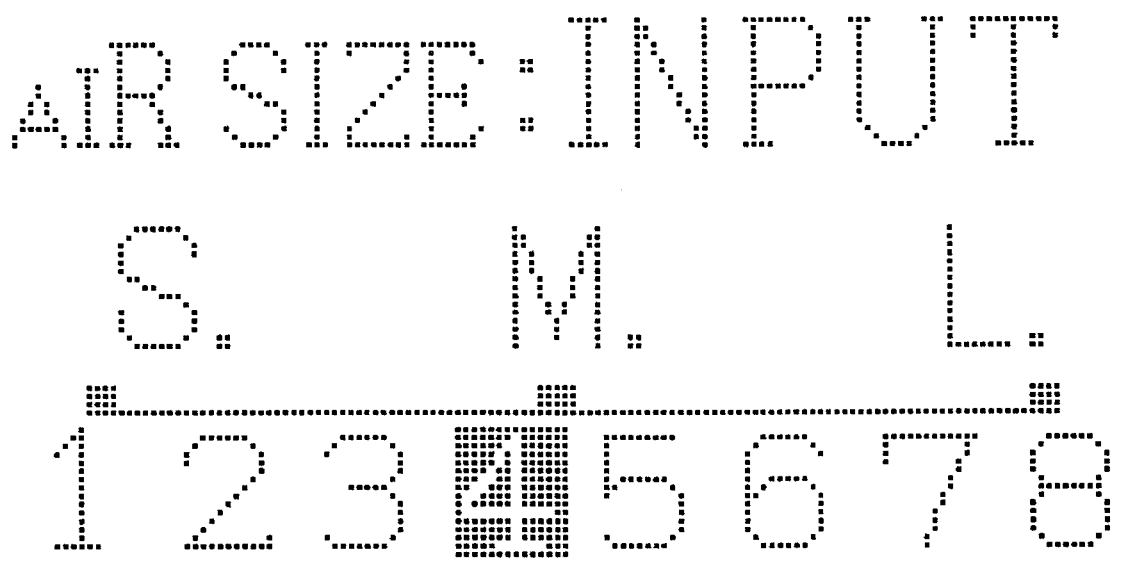

FIG. 5 is a view showing a display state of a bubble size setting screen in the transfusion device of FIGS. 1(a) and 1(b);

FIGS. 18 to 22 are views showing display states of a programming display in the transfusion device of FIG. 12; and FIGS. 23(a) and 23(b) are sectional views of a bubble sensor employed in a prior art transfusion device (already referred to).

DETAILED DESCRIPTION OF THE INVENTION

Figure 1A:
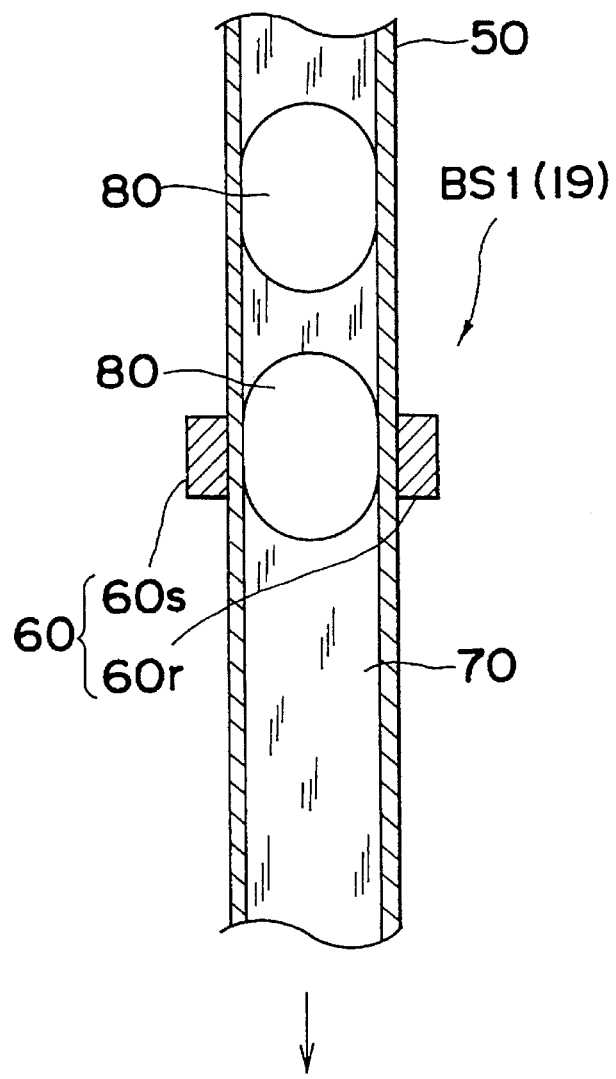
FIGS. 1(a) and 1(b) are sectional views of a bubble sensor employed in a transfusion device according to a first embodiment of the present invention.

Referring now to the drawings, there is shown in FIGS. 8 to 11, a transfusion device according to a first embodiment of the present invention. In this embodiment, the transfusion device is a positive pressure peristaltic type electromechanical intravenous infusion device which includes two pump heads and is used together with a specific transfusion set. Programming of the transfusion device is performed by a key panel. In the transfusion device, changeover from an auxiliary transfusion flow rate programmed for drug solution of a second path to a main transfusion flow rate programmed for drug solution of a first path of the same pump can be performed. In order to raise safety of a patient, various alarm functions such as detection of air bubbles, detection of upstream choking, detection of downstream choking, etc. are provided.

By depressing a power source switch 1, a power source of the transfusion device is turned on. At the time when the transfusion device is switched on, a self-test is arranged to be automatically performed temporarily. By depressing the power source switch 1 again, the power source is turned off. In a state where the transfusion device is connected to an AC power source, a built-in cell is charged regardless of whether the power source switch 1 is turned on or off.

An alarm/warning display 2 is provided for displaying all alarms and warnings regarding the transfusion device. A programming display 3 is provided for displaying all program data on transfusion such as transfusion flow rate and preset transfusion quantity inputted for each of main transfusion solution and auxiliary transfusion solution, transfused quantity, etc. Transfusion flow rate is expressed by a unit of ml/hr., while preset transfusion quantity and transfused quantity are expressed by a unit of ml. Keys 4a to 4c for main transfusion are provided for inputting transfusion flow rate and preset transfusion quantity and for starting the transfusion device in the case of feeding of only one transfusion solution. Input through manipulation of these keys can be performed only when the transfusion device is in a stop state, transfusion has been completed and the transfusion device is in main transfusion mode.

Numerical keys 5 are ten keys from "0" to "9" and all numerical data for transfusion is inputted by using these numerical keys 5. When a wrong numeral has been inputted, the display can be set to "0" by depressing a clear-key 6 and then, a correct numeral can be inputted again. When transfusion is required to be stopped manually, a stop key 7 is depressed. An alarm buzzer is adapted to be rung when no operation is performed for the transfusion device for two minutes after the transfusion device has been stopped. By stopping a buzzer stop key 8, alarm/warning sound is stopped temporarily for two minutes. However, display state of the alarm/warning display 2 does not change before and after depression of the buzzer stop key 8. Keys 9a to 9c for auxiliary transfusion are provided for inputting transfusion flow rate and preset transfusion quantity and for starting auxiliary transfusion in the case of feeding auxiliary transfusion solution. Lamps 10a to 10c are provided for displaying operational states of the transfusion device, respectively. The lamp 10a is an alarm lamp formed by a red LED and is flickered in an alarm mode so as to inform that a proper countermeasure should be taken immediately. In this case, its cause is displayed in the alarm/warding display 2. The lamp 10b is a lamp for indicating that transfusion is being performed and is formed by a green LED. This lamp 10b is turned on during transfusion and is turned off when the transfusion device is stopped. The lamp 10c is a warning lamp formed by a yellow LED and is turned on in a warning mode so as to indicate that a countermeasure should be taken. Also in this case, its cause is displayed in the alarm/warning display 2.

When a reset key 11 is depressed in a stop state of the transfusion device, transfused quantity (sum of main transfusion solution and auxiliary transfusion solution) is reset to "0". When a transfused quantity key 12 is depressed, transfused quantity (sum of main transfusion solution and auxiliary transfusion solution) is displayed and then, transfusion flow rate and preset transfusion quantity which are registered for each of main transfusion solution and auxiliary transfusion solution are displayed. If a back light key 13 is depressed when the transfusion device is being driven by the AC power source, back lights (not shown) of the alarm/warning display 2 and the programming display 3 are turned on. If the back light key 13 are depressed again, the back lights are turned off. When the transfusion device is being driven by the built-in cell, the back lights are turned on only during depression of the back light key 13.

A door handle 14a is provided for opening or closing a pump head door 14. In order to open the pump head door 14, the door handle 14a is pulled to this side while being raised sufficiently upwardly. Meanwhile, in order to close the pump head door 14, the pump head door 14 is closed by the door handle 14a while the door handle 14a is being raised and then, the door handle 14a is depressed downwardly. A lamp 15 is provided for indicating that the built-in cell is being charged and is formed by a green LED. The lamp 15 is turned on when the transfusion device is connected to the AC power source.

Figure 9:
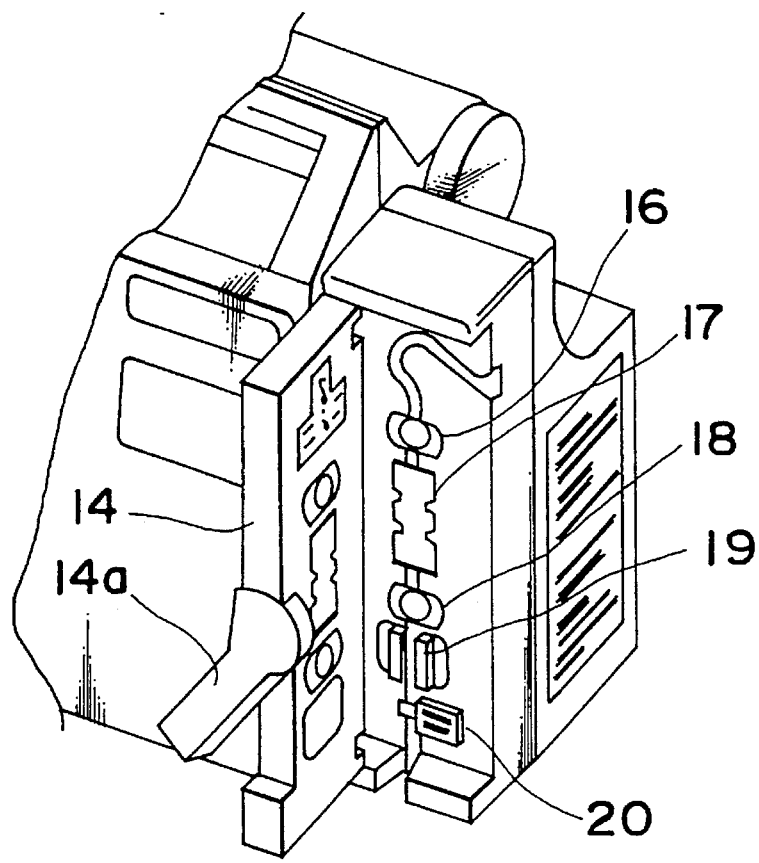
FIG. 9 is a fragmentary perspective view of the transfusion device of FIG. 8 in a state where a pump head door is opened.

In FIG. 9, a pressure drop sensor 16 is provided for detecting pressure drop due to a malfunction in a transfusion set between a vial (drug solution bag) and the transfusion device, for example, blinding of a filter. A transfusion pump mechanism 17 is of linear peristaltic type designed for a specific transfusion set. Meanwhile, a pressure rise sensor 18 is provided for detecting pressure rise in a transfusion tube due to a malfunction in a transfusion set between the transfusion device and the patient, for example, choking. A bubble sensor 19 to be described in detail later is provided for detecting not less than a preset quantity of air bubbles in the transfusion tube. A safety clamp 20 is provided for automatically closing the transfusion tube upon opening of the pump head door 14 so as to prevent gravitational downward flow of the transfusion solution.

Figure 10:
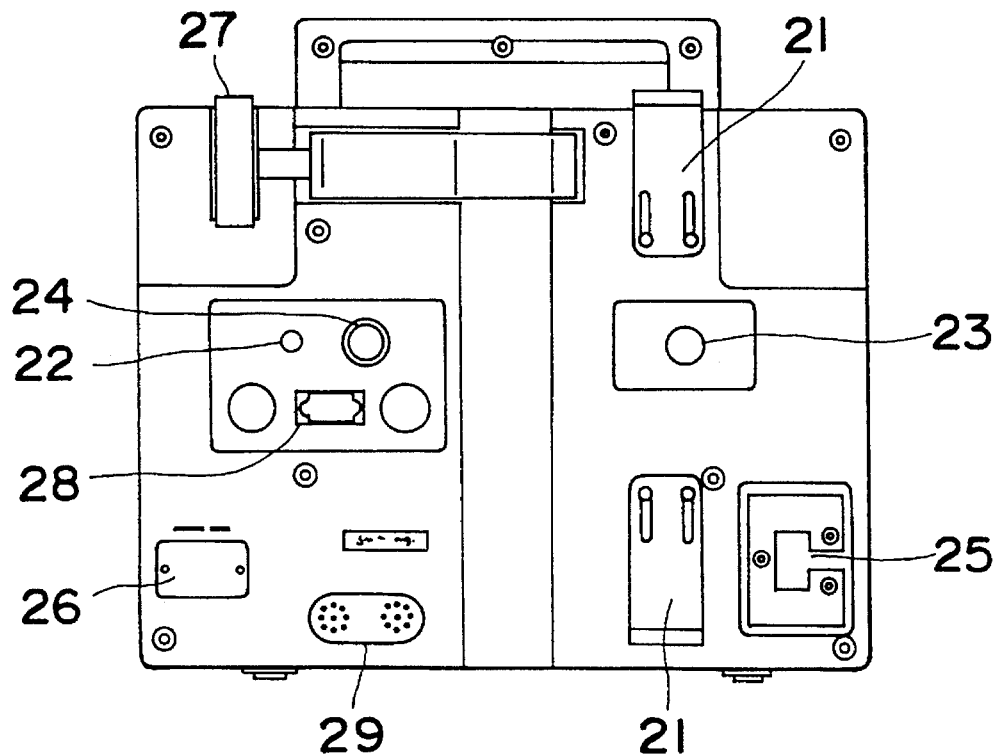
FIG. 10 is a rear elevational view of the transfusion device of FIG. 8.

In FIG. 10, reference numeral 21 denotes a power source cord holder, while reference numeral 22 denotes a panel lock switch. When the panel lock switch 22 has been depressed, the panel lock switch 22 prevents undesirable change of operation of the transfusion device even if other persons than an operator (medical practitioner or nurse) manipulate the various keys and switches inadvertently. A fuse holder 23 has a built-in fuse of specified time lag type. A sound volume knob 24 is provided for adjusting sound volume of the buzzer rung at the time of alarm or warning. A plug 25 is provided so as to be connected to a receptacle of AC 100 V. An accumulator portion 26 has a built-in lead accumulator. A pole clamp 27 is used for mounting the transfusion device on a stand. A nurse call connector portion 28 is provided for enabling nurses at a nurse center to monitor alarm/warning state of the transfusion device by using a nurse call kit. Reference numeral 29 denotes a buzzer.

Figure 11:
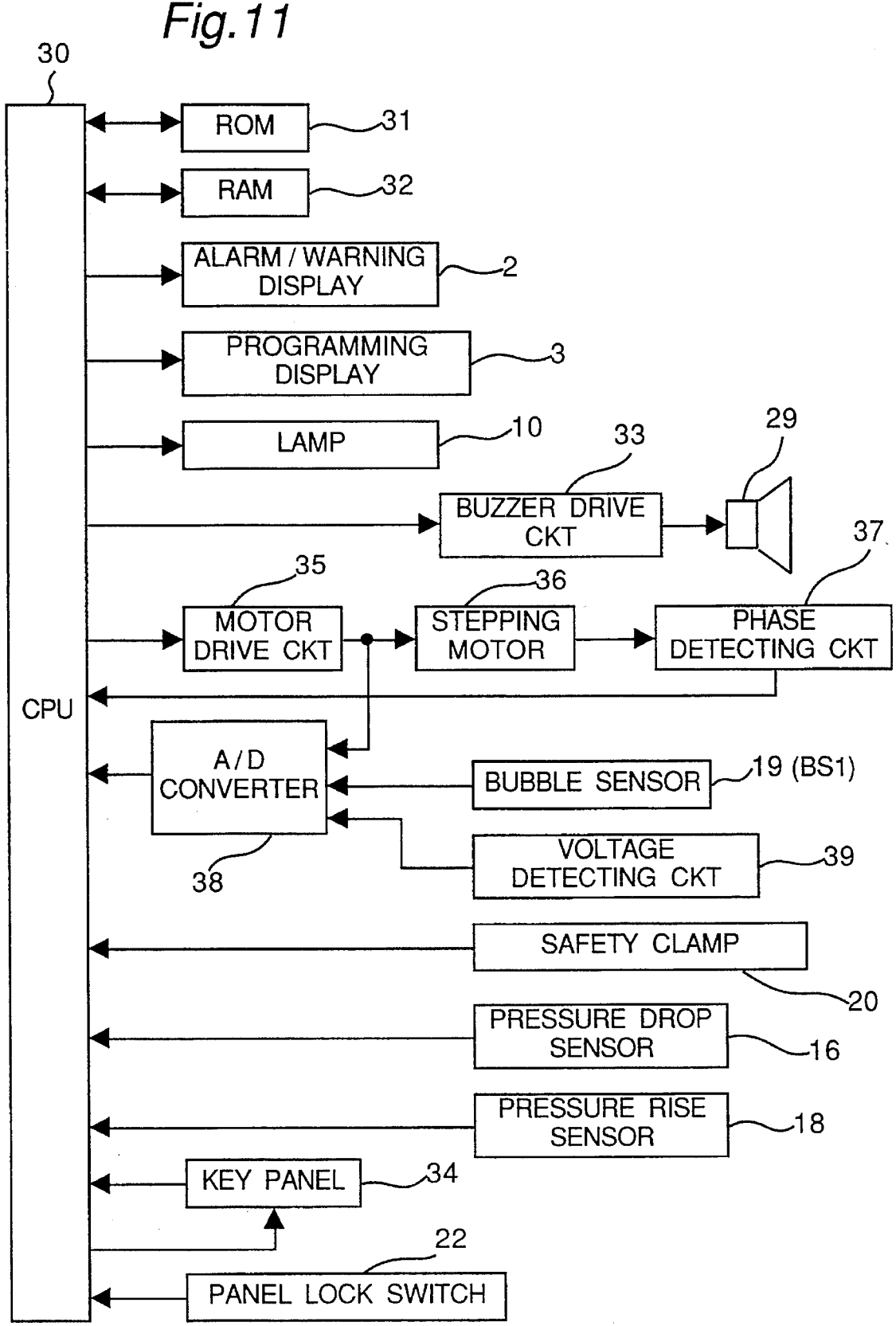
FIG. 11 is a block diagram showing an electrical configuration of the transfusion device of FIG. 8.

In FIG. 11, a CPU 30 is reset upon turning on of the power source and controls the transfusion device as a whole. A ROM 31 is provided for storing program data necessary for functioning of the transfusion device. Meanwhile, a RAM is provided for storing various data such as size of air bubbles to be detected, transfusion rate, transfusion quantity, pressurization feed rate, permissible quantity of air bubbles mixed into a unit volume of the transfusion solution and permissible quantity of air bubbles mixed into the transfusion solution during a unit time period. This RAM 32 is backed up by a battery even when the power source is turned off. As described above, the 10 alarm/warning display 2, the programming display 3, a lamp constituted by the lamps 10a to 10c, the pressure drop sensor 16, the pressure rise sensor 18, the bubble sensor 19, the safety clamp 20, the panel lock switch 22 and the buzzer 29 are provided.

Reference numeral 33 denotes a drive circuit for the alarm/warning buzzer. A key panel 34 is provided with the power source switch 1, the keys 4a to 4c for main transfusion, the numerical key 5, the clear key 6, the stop key 7, the buzzer stop key 8, the keys 9a to 9c for auxiliary transfusion, the reset key 11, the back light key 13, etc. The transfusion pump mechanism 17 includes a motor drive circuit 35, a stepping motor 36, a phase detecting circuit 37 for detecting rotational phase of the stepping motor 36, etc. Reference numeral 38 denotes an analog-digital converter, reference numeral 39 denotes a voltage detecting circuit for detecting voltage of the cell. The motor drive circuit 35 controls the stepping motor 35 on the basis of commands from the CPU 30, while the phase detecting circuit 37 detects rotational phase of the stepping motor 36 by using a photointerrupter and sends the rotational phase to the CPU 30. A plurality of eccentric cams whose phases deviate slightly from each other are mounted on an output shaft of the stepping motor 36 closely in an axial direction of the output shaft and a peristaltic finger for pressing a transfusion tube 50 (FIGS. 1(a) and 1(b)) to be described later is fixed to an outer periphery of each of the eccentric cams. The analog-digital converter 38 converts state of the stepping motor 36, output level of the bubble sensor 19 and output value of the voltage detecting circuit 39 from analog amount to digital data so as to transmit the digital data to the CPU 30.

Hereinbelow, construction of a bubble sensor BS1 of the transfusion device is described with reference to FIGS. 1(a) and 1(b). This bubble sensor BS1 corresponds to the bubble sensor 19 of FIG. 11. In FIG. 1, the drug solution bag is coupled with one end of the transfusion tube 50, while an injection needle is coupled with the other end of the transfusion tube 50. The bubble sensor BS1 is attached to an intermediate portion of the transfusion tube 50. The bubble sensor BS1 is formed by an ultrasonic sensor 60 including an ultrasonic transmitter 60s and an ultrasonic receiver 60r. The ultrasonic transmitter 60s and the ultrasonic receiver 60r are brought into contact with an outer peripheral surface of the transfusion tube 50 so as to confront each other in a radial direction of the transfusion tube 50. In FIG. 1, reference numeral 70 denotes transfusion solution (drug solution) flowing in the transfusion tube 50, while reference numeral 80 denotes air bubbles mixed into the transfusion solution 70. The transfusion tube 50 described above is set in the transfusion pump mechanism 17 of the transfusion device. The transfusion tube 50 has a diameter of 0.25 cm and a cross-sectional area of 0.05 cm$^2$.

Figure 1B:
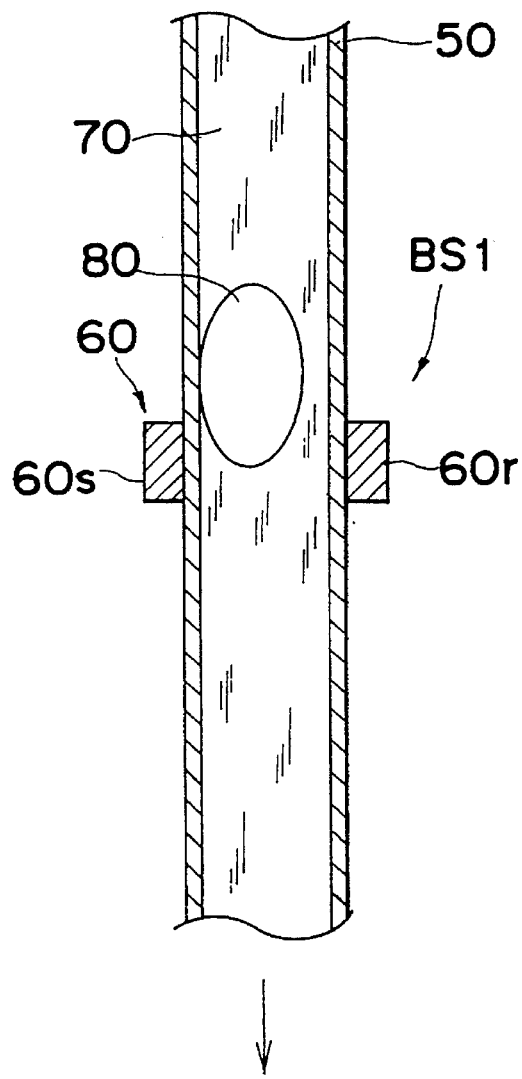

In FIG. 1(a), two air bubbles 80 expanded to full cross section of the transfusion tube 50 and located adjacent to each other flow in the transfusion tube 50. On the other hand, in FIG. 1(b), one air bubble 80 smaller than cross section of the transfusion tube 50 flows in the transfusion tube 50. As described later, it is so arranged in this embodiment that by measuring cross-sectional area of the air bubbles 80 and integrating the cross-sectional area of the air bubbles 80 in flow direction of the transfusion tube 50, volume of the air bubbles 80 is measured quite accurately. When only the transfusion solution 70 flows in the transfusion tube 50 relative to an ultrasonic path connecting the ultrasonic transmitter 60s and the ultrasonic receiver 60r, ultrasonic wave is not damped so much and thus, reaches the ultrasonic receiver 60r, thereby resulting in output of the ultrasonic receiver 60r being maintained at a high level. When the air bubbles 80 mixed into the transfusion solution 70 passes through the ultrasonic path, ultrasonic wave is damped by the air bubbles 80, thereby resulting in drop of output level of the ultrasonic path. Degree of drop of output level of the ultrasonic path depends on cross-sectional area of the air bubbles 80. An output signal of analog amount from the ultrasonic sensor 60 is converted into digital data by the analog-digital converter 38 so as to be delivered to the CPU 30.

Figure 2:
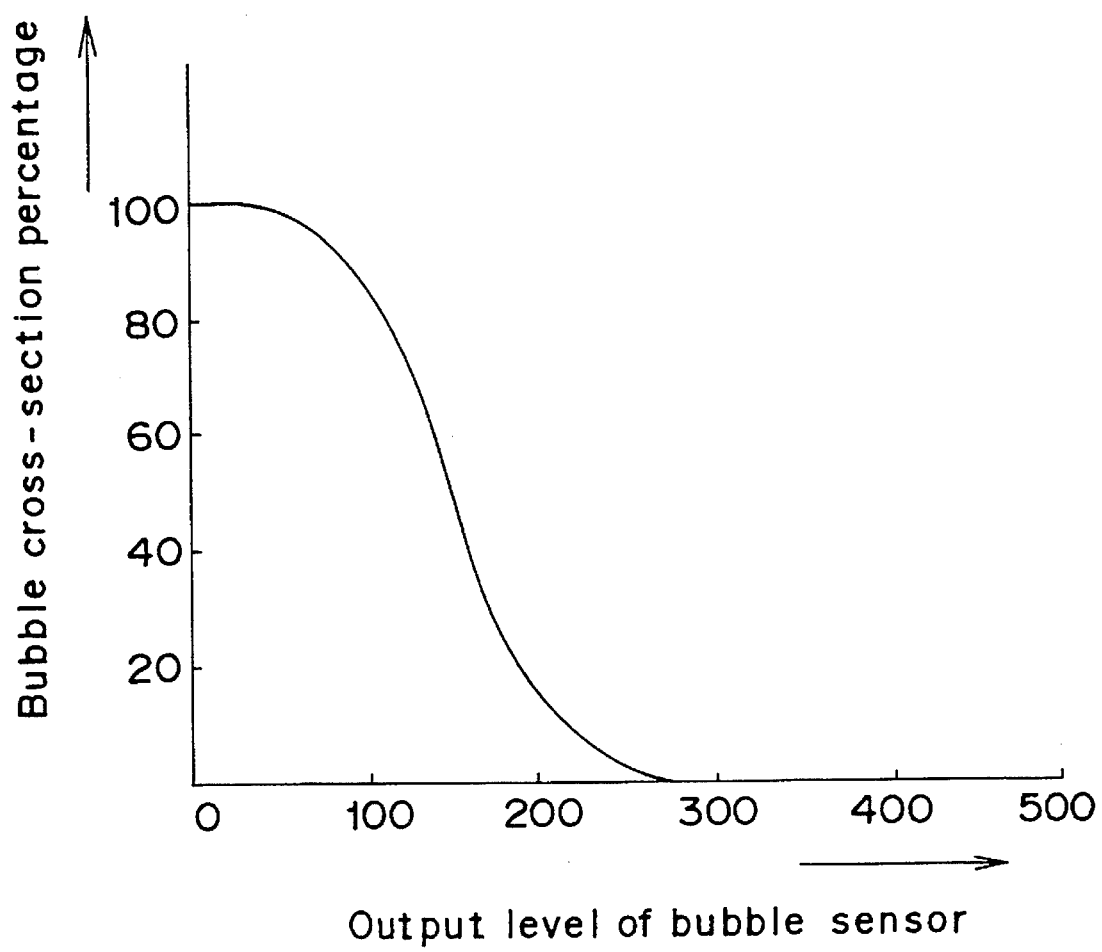
FIG. 2 is a characteristic diagram showing relation between output level of the bubble sensor and bubble cross-section percentage in the transfusion device of FIGS. 1(a) and 1(b)

FIG. 2 shows relation between output level of the bubble sensor BS1 and ratio of a cross-sectional area $S_B$ of the air bubbles 80 to a cross-sectional area $S_T$ of the transfusion tube 50 (bubble cross-section percentage). Output level of the bubble sensor BS1 and bubble cross-section percentage correspond to each other one-to-one. For example, when output level of the bubble sensor BS1 exceeds 300, bubble cross-section percentage is 0% which indicates that the air bubbles 80 do not pass through the ultrasonic path. Meanwhile, when output level of the bubble sensor BS1 is 150, bubble cross-section percentage is 50%. Furthermore, when output level of the bubble sensor BS1 is 100, bubble cross-section percentage is 80% which corresponds to FIG. 1(b). When output level of the bubble sensor BS1 is 20, bubble cross-section percentage is 100% which corresponds to FIG. 1(a).

Figure 3:
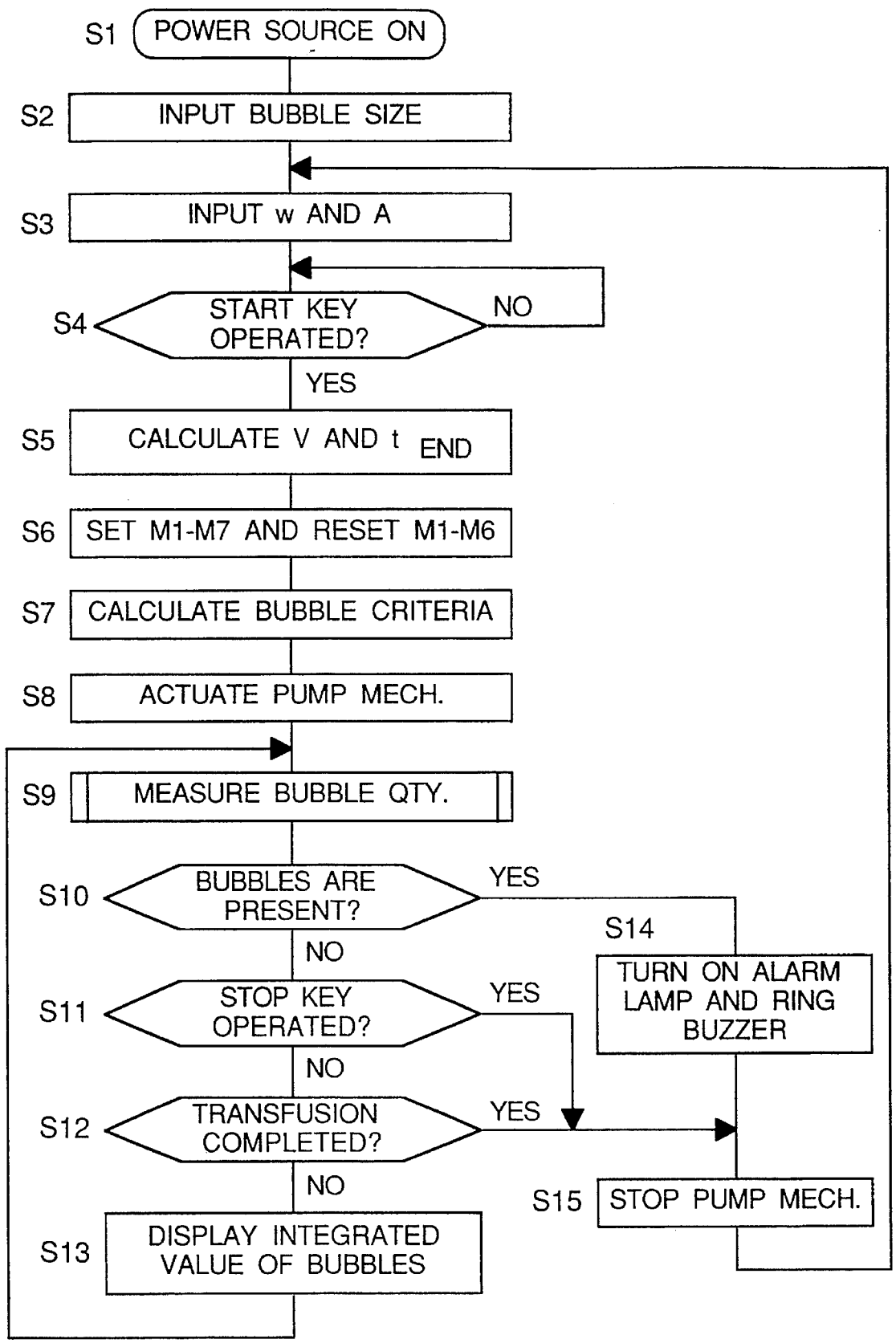
FIG. 3 is a flow chart explanatory of operation of the transfusion device of FIGS. 1(a) and 1(b)

Hereinbelow, operations of bubble detection in the transfusion device of the above described arrangement are described with reference to flow charts of FIGS. 3 and 4. By turning on the power source at step S1, the subsequent steps S2 and so on are executed. At step S2, a bubble size setting screen shown in FIG. 5 is displayed in the programming display 3. Thus, by using the numerical keys 5 and the clear key 6 if necessary, the operator inputs size $B_B$ of the air bubbles 80 to be detected. In this embodiment, size of the air bubbles 80 can be set in eight stages as shown by the lowermost row in FIG. 5. In FIG. 5, the uppermost row means "input of air size", namely, input of size of the air bubbles 80. Meanwhile, characters "S.", "M." and "L" in the middle row of FIG. 5 mean "small", "medium" and "large" sizes of the air bubbles 80, respectively. An inputted numeral indicative of size of the air bubbles 80 is displayed in the bubble size setting screen through black-and-white inversion. Data of the inputted size $B_B$ of the air bubbles 80 is stored in the RAM 32.

Then, at step S3, transfusion rate (transfusion flow rate) w (ml/hr.) and transfusion quantity (preset transfusion quantity) A (ml) are inputted by using the numerical keys 5. Data of the inputted transfusion rate w and the transfusion quantity A is stored in the RAM 32. After the key 4c for starting transfusion of the main transfusion solution has been depressed at step S4, the program flow proceeds to step S5. At step S5, the CPU 30 calculates a pressurization feed rate V (cm/sec.) and a time point $t_{END}$ of end of transfusion. The pressurization feed rate V is calculated by the following equation based on a transfusion rate W (ml/sec.) converted from the transfusion rate w (ml/sec.) and the cross-sectional area $S_T$ (cm$^2$) of the transfusion tube 50.

$$V = W/S_T$$

Namely, this means the pressurization feed rate (cm/s.)= {transfusion rate W (ml/s.)}/{cross-sectional area of tube (cm$^2$)}. In this embodiment, the cross-sectional area $S_T$ of the transfusion tube 50 is 0.05 cm$^2$. The time point $t_{END}$ is calculated by the following equation from a present time point t0, the transfusion quantity A (ml) and the transfusion rate W (ml/sec.).

$$t_{END} = t_0 + A/W$$

Namely, this means the time point of end of transfusion= the current time point+{transfusion quantity (ml)/transfusion rate (ml/s.)}.

Subsequently, at step S6, the CPU 30 sets memories M1 to M7 necessary for detection of the air bubbles 80 as follows. This setting is performed in the RAM 32.

| [Memory] | [Function] | [Capacity (words)] |
|---|---|---|
| M1 | Memory for integrated value of air bubbles | 1 |
| M2 | Loop memory for quantity of air bubbles in 100 µl | 10 |
| M3 | Pointer for M2 | 1 |
| M4 | Loop memory for quantity of air bubbles per minute | 60 |
| M5 | Pointer for M4 | 1 |
| M6 | Memory for integration at an interval of 10 min. for display | 128 |
| M7 | Memory for sampling interval | 1 |

Each time output level of the bubble sensor BS1 is sampled, the memory M1 for integrated value of air bubbles performs addition of a processed value of the output level. The loop memory M2 for quantity of air bubbles in 100 µl is a memory array required for checking permissible quantity of air bubbles mixed into a predetermined quantity of 100 µl of the transfusion solution so as to read or write a value indicated by the pointer M3 for the loop memory M2. The pointer M3 for the loop memory M2 is provided for indicating a location read or written by the loop memory M2 and assumes values from 0 to 9. A value of the loop memory M2, which is indicated by the pointer M3, is expressed by "M2[M3]" (FIG. 6) to be described later. The loop memory M4 for quantity of air bubbles per minute is a memory array required for checking permissible quantity of air bubbles mixed into the transfusion solution per minute so as to read or write a value indicated by the pointer M5 for the loop memory M4. The pointer M5 for the loop memory M4 is provided for indicating a location read or written by the loop memory M4 and assumes values from 0 to 59. A value of the loop memory M4, which is indicated by the pointer M5, is expressed by "M4[M5]". The memory M6 for integration at an interval of 10 min. for display is a memory for storing quantity of air bubbles at an interval of 10 min. The memory M7 for sampling interval indicates a sampling interval of the bubble sensor BS1. The sampling interval is determined by the following equation.

Sampling interval (sec.)=1/{transfusion rate (ml/s.)×100}

For example, when the transfusion rate is 0.5 ml/s., the sampling interval is 1/50 s. Quantity of the transfusion solution flowing during this sampling interval is 0.5 (ml/ s.)×1/50 (s.)=1/100 (ml)=10 µl. Namely, the sampling interval corresponds to a period during which 10 µl of the transfusion solution passes through the bubble sensor BS1. In other words, regardless of transfusion rate, air bubbles are sampled each time 10 µl of the transfusion solution passes through the bubble sensor BS1. At step S6, not only setting of the memories M1 to M7 is performed but the memories M1 to M6 other than the memory M7 for sampling interval are reset to "0".

At step S7, the CPU 30 performs calculation of bubble criteria. Namely, on the basis of the size $B_B$ of the air bubbles 80 set at step S2 and the transfusion rate W set at step S3, the CPU 30 calculates permissible quantity of the air bubbles 80 mixed into a predetermined quantity of 100 μl of the transfusion solution to be detected and permissible quantity of the air bubbles 80 mixed into the transfusion solution during a predetermined period of 1 min. and stores the calculation results in the RAM 32 as permissible air bubble quantities $\alpha_{REF}$ and $\alpha_{REF}$, respectively.

Subsequently, at step S8, the CPU 30 controls the motor drive circuit 35 so as to drive the stepping motor 36 such that the transfusion pump mechanism 17 is actuated. Thus, the transfusion tube 50 interposed between a plurality of the peristaltic fingers mounted on the output shaft of the stepping motor 36 and a backing plate is squeezed peristaltically by sequential rotation of the peristaltic fingers such that pressurization feed of the transfusion solution 70 in the transfusion tube 50 is started. After pressurization feed of the transfusion solution 70 has been started, the program flow proceeds to step S9 at which the CPU 30 determines quantity of the air bubbles 80 obtained by the bubble sensor BS1.

Figure 4:
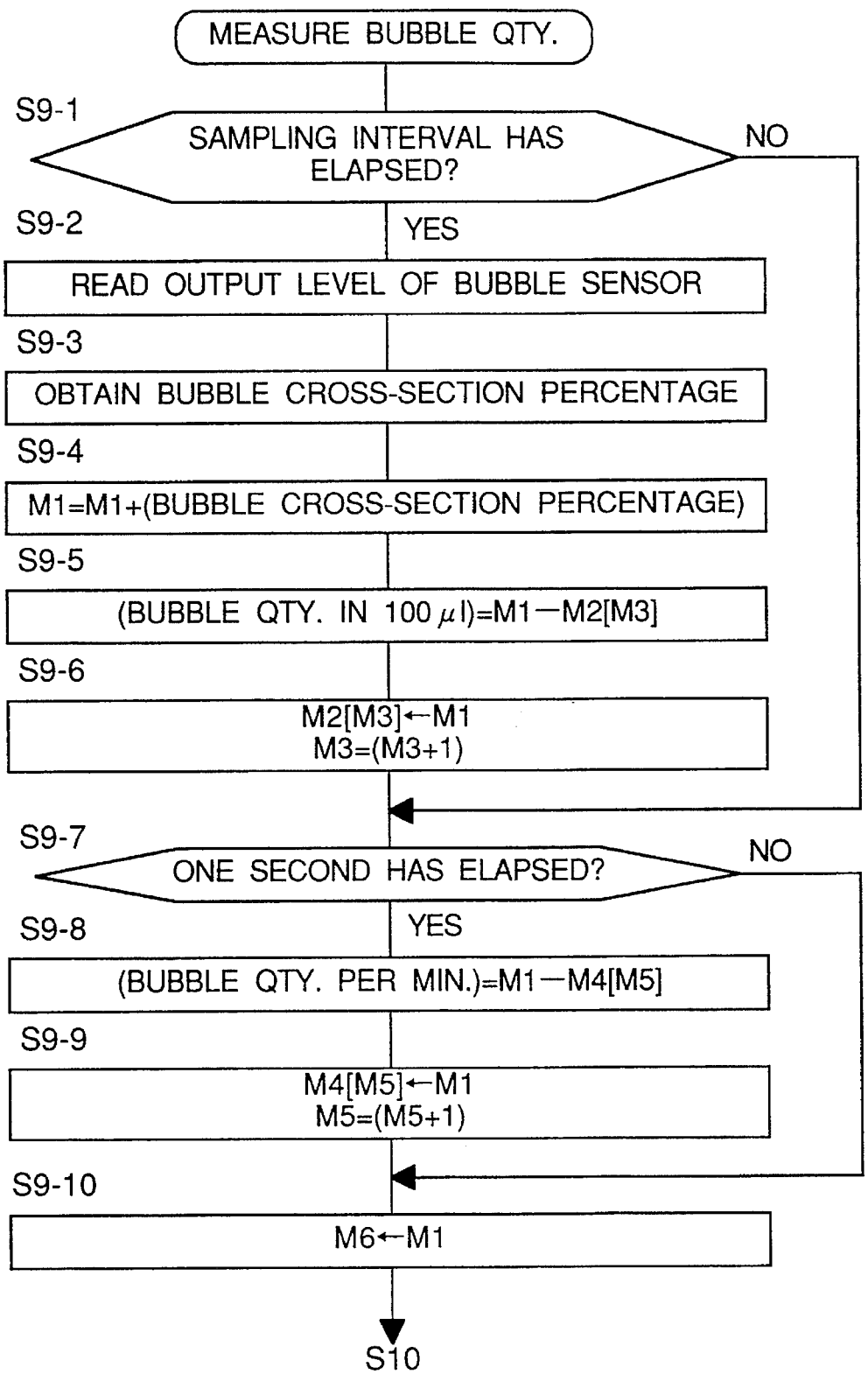
FIG. 4 is a flow chart showing a bubble quantity measuring step S9 in FIG. 3 in detail.

FIG. 4 shows operation of this step S9 in detail. Hereinbelow, steps S9-1 to S9-10 of FIG. 4 are described. Initially, at step S9-1, it is judged whether or not the sampling interval stored in the memory M7 for sampling interval has elapsed at a present time point from the previous sampling time point. In the case of "NO" at step S9-1, the program flow skips to step S9-7. In case step S9-1 is executed for the first time and in the case of "YES" at step S9-1, the program flow proceeds to step S9-2. At step S9-2, output level of the bubble sensor BS1 is read through the analog-digital converter 38 and is set as an output value of the bubble sensor BS1. Thereafter, at step S9-3, ratio of the cross-sectional area $S_B$ of the air bubbles 80 to the cross-sectional area $S_T$ of the transfusion tube 50, i.e. bubble cross-section percentage described earlier with reference to FIG. 2 is obtained. Relation between output value of the bubble sensor BS1 and bubble cross-section percentage is preliminarily stored as a table in the ROM 31 so as to correspond to characteristics shown in FIG. 2.

Since the sampling interval is a period during which 10 μl of the transfusion solution passes through the bubble sensor BS1 as described above, bubble cross-section percentage represents ratio of volume occupied by air bubbles in 10 μl of the transfusion solution located upstream and downstream of the bubble sensor BS1 to 10 μl of the transfusion solution. Since bubble cross-section percentage is expressed in percent, quotient obtained by dividing the bubble cross-section percentage by 10 is detected quantity of air bubbles expressed in μl.

Subsequently, at step S9-4, the CPU 30 adds to the memory M1, bubble cross-section percentage (i.e., detected quantity of air bubbles) obtained at step S9-3. As a result, the integrated value M1 of air bubbles represents a product (in μl) of 10 by a cumulative sum of detected quantity of air bubbles from start of transfusion. Then, at step S9-5, by reducing from the integrated value M1 of air bubbles up to the present, M2[M3] which is the integrated value of air bubbles preceding through 100 μl, a product (in μl) of 10 by quantity of air bubbles mixed into 100 μl of the latest transfusion solution is obtained and this result is set as quantity of air bubbles in 100 μl of the transfusion solution.

Figure 6:
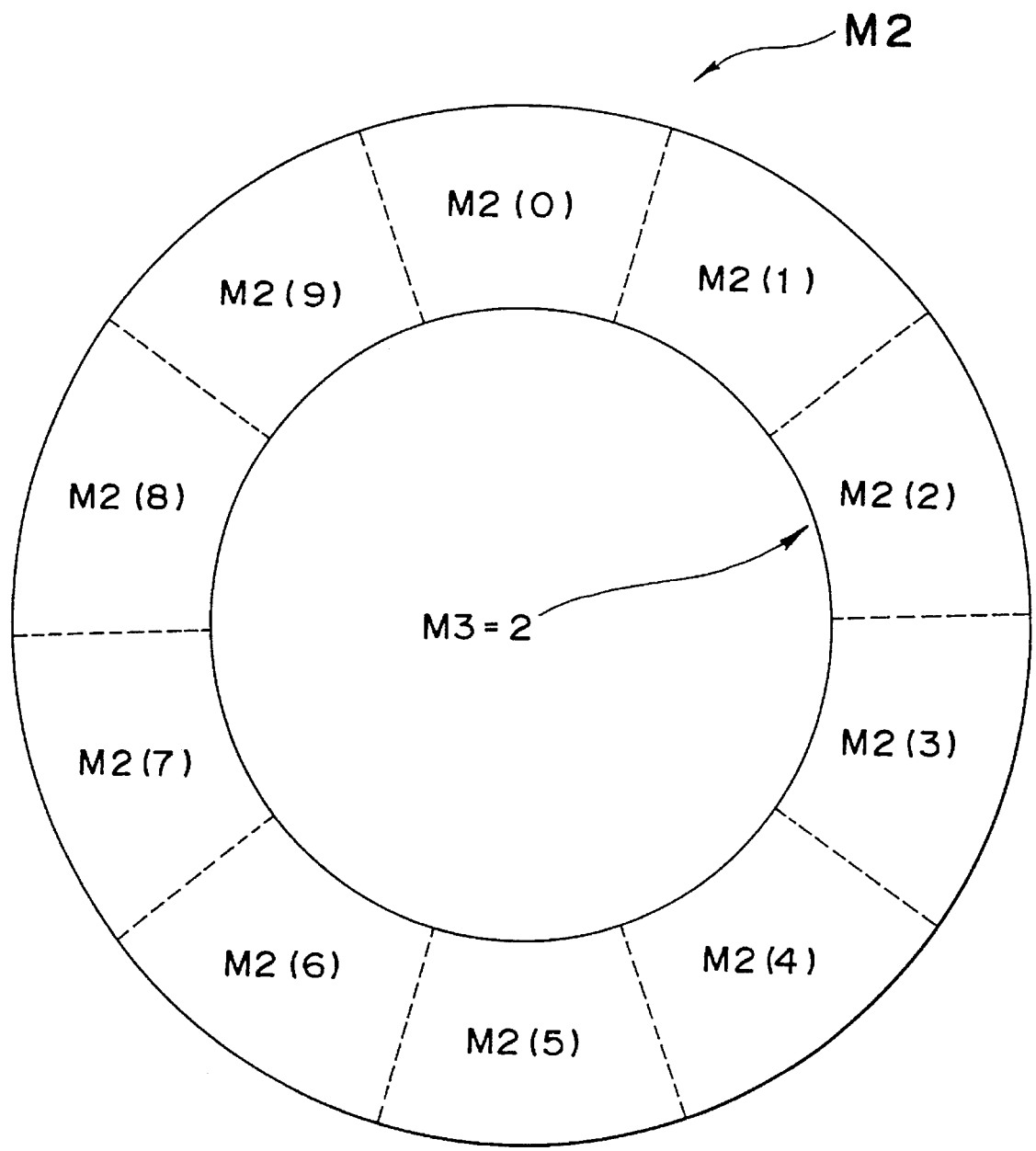
FIG. 6 is a view explanatory of a loop memory for quantity of air bubbles mixed into 100 µl of transfusion solution in the transfusion device of FIGS. 1(a) and 1(b)

Here, the array M2[M3] is described. The array M2[M3] is a loop memory in which integrated values of air bubbles mixed into previous 100 μl of the transfusion solution are arranged in a loop at an interval of 10 μl as shown in FIG. 6. Therefore, if setting is performed such that after integrated value of air bubbles has been written at the M3-th M2, M3 denotes the next address of M2, the M3-th M2 is integrated value of air bubbles preceding through 100 μl. Accordingly, at step S9-6, the integrated value M1 of air bubbles obtained at step S9-5 is substituted for M2[M3] and an increment of "1" is imparted to the pointer M3 for the loop memory M2. In this increment, the remainder of 10 is obtained such that the increment result is reinstated to "0" when the increment result is 10 or more. Namely, when 9+1=10, 10−10=0 is obtained. Meanwhile, M2[M3] obtained at step S9-6 is subsequently subtracted at step S9-5 at which 100 μl of the transfusion solution has flown through the bubble sensor BS1.

When the program flow proceeds to step S9-7 from step S9-1 or S9-6, it is judged whether or not one second has elapsed from a time point when quantity of air bubbles per minute was written in the loop memory M4. In the case of "NO" at step S9-7, the program flow skips to step S9-10 even if sampling has been performed at steps S9-2 to S9-4. In case step S9-7 is executed for the first time and in the case of "YES" at step S9-7, the program flow proceeds to step S9-8 even if sampling has not been performed at steps S9-2 to S9-4. At step S9-8, by subtracting from the integrated value M1 of air bubbles obtained at the latest step S9-4, M4[M5] which is integrated value of air bubbles obtained one minute before, a product (in μl) of 10 by quantity of air bubbles mixed into the transfusion solution during the latest one minute is obtained and this result is set as quantity of air bubbles mixed into the transfusion solution per minute.

Here, the array M4[M5] is described. The array M4[M5] is a loop memory in which integrated values of air bubbles during the previous one minute (60 sec.) are arranged in a loop at an interval of one sec. Therefore, if setting is performed such that after integrated value of air bubbles has been written at the M5-th M4, M5 denotes the next address of M4, the M5-th M4 is integrated value of air bubbles obtained one minute before. Accordingly, at step S9-9, the latest integrated value M1 of air bubbles is substituted for M4[M5] and an increment of "1" is imparted to the pointer M5 for the loop memory M4. In this increment, the remainder of 60 is obtained such that the increment result is reinstated to "0" when the increment result is 60 or more. Namely, when 59+1=60, 60−60=0 is obtained. Meanwhile, M4[M5] obtained at step S9-9 is subsequently subtracted at step S9-8 at which one minute has elapsed.

When the program flow proceeds to step S9-10 from step S9-7 or S9-9, the integrated value M1 of air bubbles at the present time point obtained at step S9-4 is substituted for the memory M6 indicative of integrated value of air bubbles at an interval of 10 min. Then, the program flow proceeds to step S10 of FIG. 3.

At step S10, it is judged whether or not air bubbles are present or not. Namely, it is judged whether quantity of air bubbles mixed into 100 μl of the transfusion solution obtained at step S9-5 exceeds the bubble criterion obtained at step S9-7, i.e. the permissible quantity $\alpha_{REF}$ of air bubbles mixed into 100 μl of the transfusion solution and whether or not quantity of air bubbles mixed into the transfusion solution per minute obtained at step S9-8 exceeds the bubble criterion obtained at step S7, i.e. the permissible quantity $\beta_{REF}$ of air bubbles mixed into the transfusion solution per minute. When $M2 \leq \alpha_{REF}$ and $M4 \leq \beta_{REF}$, it is judged that air bubbles are absent, so that the program flow proceeds to step S11 at which it is judged whether or not the stop key 7 has been depressed. In the case of "YES" at step S11, the program flow proceeds to step S15 at which the stepping motor 36 is stopped by controlling the motor drive circuit 35 so as to stop the transfusion pump mechanism 17 such that transfusion is suspended. On the other hand, in the case of "NO" at step S11, the program flow proceeds to step S12 at which it is judged whether or not transfusion has been completed, namely, time has reached the time point $t_{END}$ of end of transfusion obtained at step S5. In the case of "YES" at step S12, the program flow proceeds to step S15 at which transfusion is stopped by stopping the stepping motor 36. On the contrary, in the case of "NO" at step S12, the program proceeds to step S13.

At step S13, the CPU 30 performs graphic display of the contents of the memory M6, i.e. integrated value of air bubbles at an interval of 10 min. in the programming display 3. The first value M6[0] of the array represents quantity of air bubbles for initial 10 min. Subsequent quantity of air bubbles T min. (T=10, 20, 30, 40, ---) after start of transfusion is given by the following equation.

(Integrated value of air bubbles at an interval of 10 min.) =M6[T/10]–M6[T/10–1]

Figure 7:
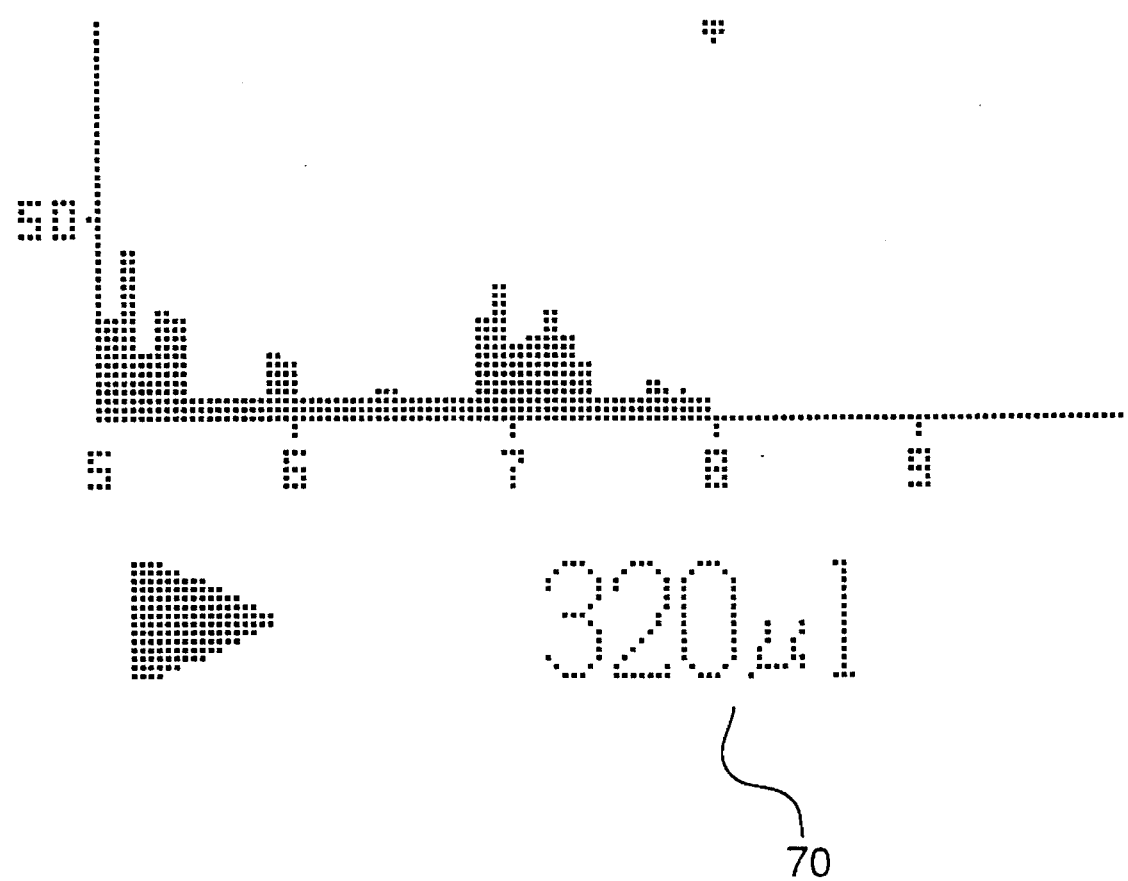
FIG. 7 is a view showing a display state of a screen for displaying quantity of air bubbles in transfusion solution in the transfusion device of FIGS. 1(a) and 1(b)
Figure 8:
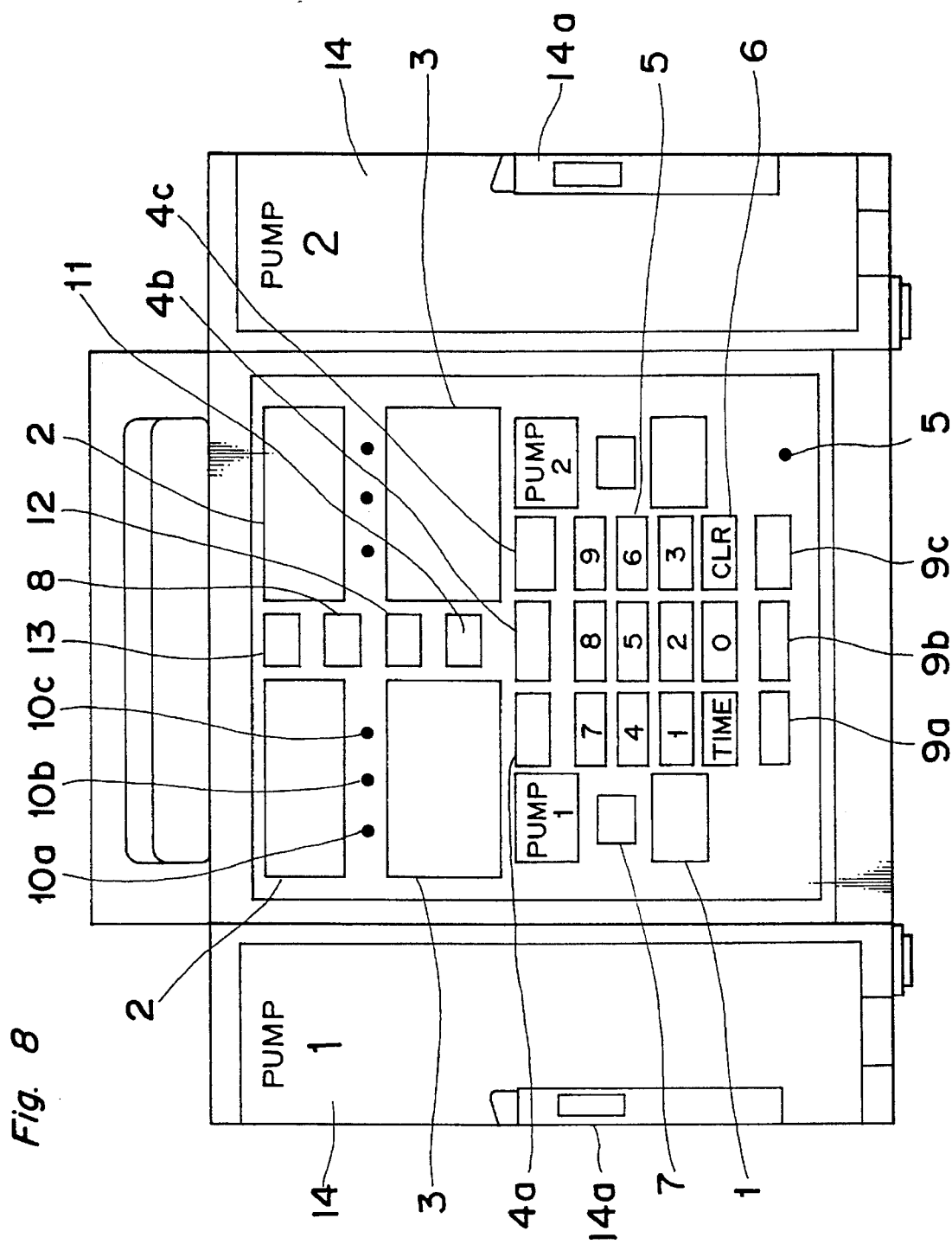
FIG. 8 is a front elevational view of the transfusion device of FIGS. 1(a) and 1(b)

This value is graphically shown in FIG. 7. In FIG. 7, the axis of abscissa represents time, while the axis of ordinate represents quantity of air bubbles. The numeric having reference numeral 70 shows cumulative quantity of air bubbles in the transfusion solution after start of transfusion. After step S13, the program flow returns to the routine of step S9 (FIG. 4) for measuring quantity of air bubbles and the same operation as described above is repeated subsequently.

On the contrary, when $M2>\alpha_{REF}$ or $M4>\beta_{REF}$ at step S10, it is judged that air bubbles are present, so that the program flow proceeds to step S14. At step S14, a warning display of "mixing of air bubbles" is made in the alarm/warning display 2, the alarm lamp 10a is turned on and the buzzer 29 is rung so as to emit a warning sound. Then, at step S15, the stepping motor 36 is stopped by controlling the motor drive circuit 35 so as to stop the transfusion pump mechanism 17 such that transfusion is suspended.

In the first embodiment, if sampling speed is increased, it becomes possible to detect even minute air bubbles. Meanwhile, even if scatter of transfusion rate occurs due to states of the transfusion pump mechanism 17, it is possible to deal with this scatter by adjusting sampling speed in accordance with the scatter. Furthermore, when reliability of the transfusion device is raised, a plurality of the bubble sensors BS1 may be prepared such that outputs of the respective ultrasonic receivers are subjected to identical processing.

Figure 12:
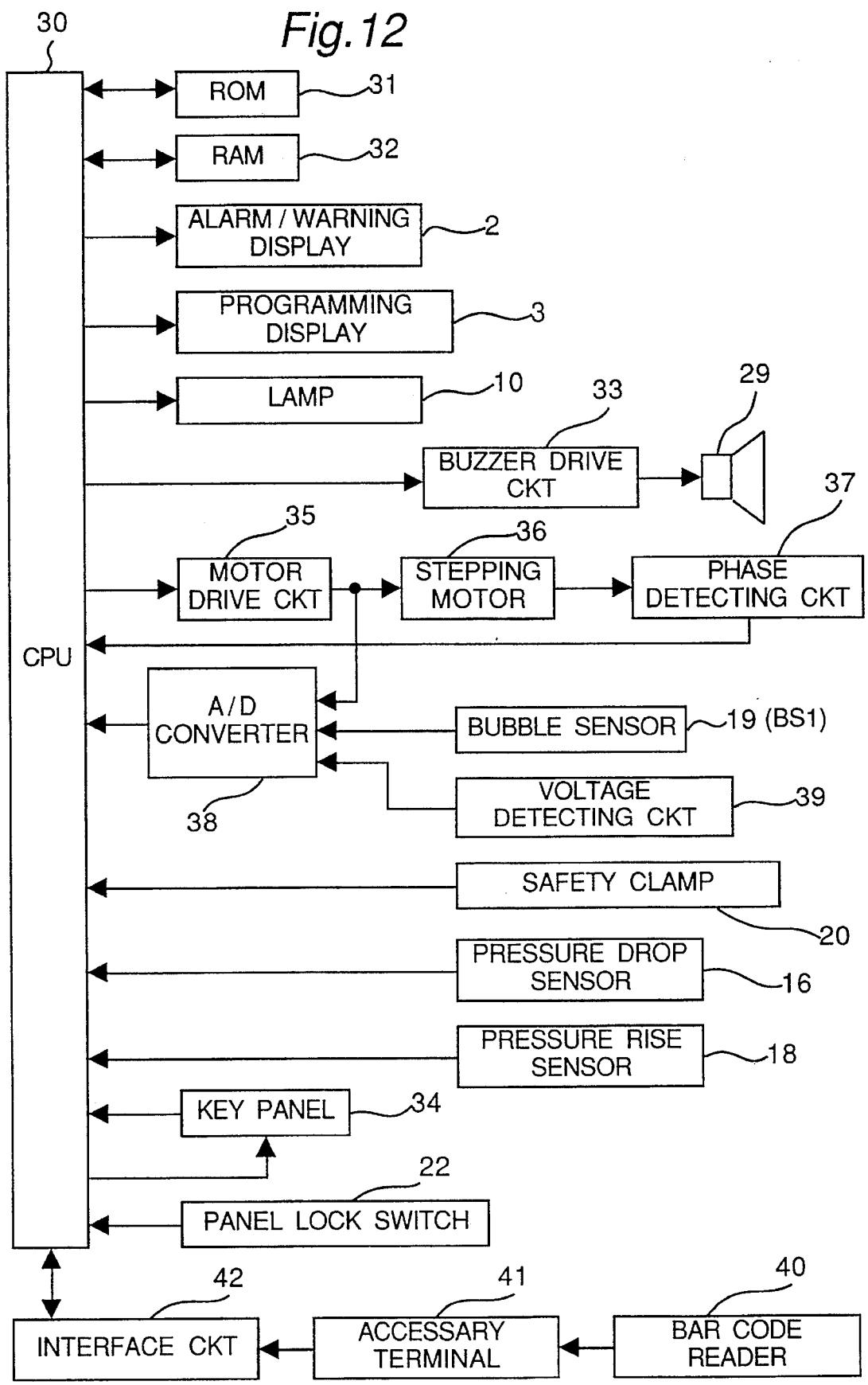
FIG. 12 is a block diagram showing an electrical configuration of a transfusion device according to a second embodiment of the present invention.

FIG. 12 shows an electrical configuration of a transfusion device (positive pressure peristaltic type intravenous infusion device) according to a second embodiment of the present invention. Since this transfusion device has constructions similar to those of FIGS. 8, 9 and 10 of the transfusion device of the first embodiment, description of the constructions is abbreviated for the sake of brevity. The transfusion device includes a bar code reader 40 acting as an optical data reader, an accessary terminal 41 and an interface circuit 42 for the bar code reader 40. The bar code reader 40 is connected to the interface circuit 42 through the accessary terminal 41 and the interface circuit 42 is, in turn, connected to the CPU 30. When a power source of the transfusion pump mechanism 17 is in ON state, the interface circuit 42 reads data from the bar code reader 40 at all times and the latest data read from the bar code reader 40 by the interface circuit 42 is stored in a buffer of the interface circuit 42 so as to be transferred to the CPU 30 upon request from the CPU 30. Meanwhile, a resetting command is given to the interface circuit 42 by the CPU 30, data of the buffer of the interface circuit 42 is erased. Since other constructions of the transfusion device are similar to those of the transfusion device of the first embodiment, the description is abbreviated for the sake of brevity.

Bar codes to be read by the bar code reader 40 are divided into two kinds, i.e. one printed on a drug container and the other printed on a prescription, etc.

(1) Contents of bar code on drug container (Drug container codes)

Drug container code ID, drug code, Maximum transfusion quantity, Maximum transfusion period, Maximum transfusion rate, Minimum transfusion quantity, Minimum transfusion period, Minimum transfusion rate, Container capacity (2) Contents of bar code on prescription, etc.
(Prescription codes)

Prescription code ID, Drug code {[Drug code] . . .}, [Transfusion quantity], [Transfusion rate], [Transfusion starting time point]

The drug container code ID is a specific value indicating that this code is the drug container code, while the prescription code is a specific value indicating that this code is the prescription code. The drug code is a code for identifying kind of each drug, which is attached to the drug. The drug code of the prescription is capable of designating two or more kinds of drugs. The maximum transfusion quantity is a maximum value of transfusion quantity, at which the drug is allowed to be transfused into a body. The maximum transfusion period is a maximum value of transfusion period, at which the drug is allowed to be transfused into a body. The maximum transfusion rate is a maximum value of transfusion rate, at which the drug is allowed to be transfused into a body. The minimum transfusion quantity is a minimum value of transfusion quantity, at which the drug is allowed to be transfused into a body. The minimum transfusion period is a minimum value of transfusion period, at which the drug is allowed to be transfused into a body. The minimum transfusion rate is a minimum value of transfusion rate, at which the drug is allowed to be transfused into a body. The container capacity is a capacity of the container containing the drug. The transfusion quantity is a transfusion quantity indicated by the prescription. The transfusion rate is a transfusion rate indicated by the prescription. The transfusion starting time point is a transfusion starting time point indicated by the prescription. When time has reached this time point, the transfusion device starts transfusion. The items enclosed by brackets "[ ]" can be deleted as required. The symbol ". . ." represents input repeated if necessary.

In the prescription code, when a plurality of drugs are transfused at a time, the same number of drug codes can be stored. Meanwhile, in the prescription code, a plurality of transfusions are performed continuously, the same number of prescription codes should be prepared. Furthermore, when the prescription code or the drug container code is not contained in one bar code, the single prescription code or the single drug container code may be composed of a plurality of bar codes.

Hereinbelow, operation of the transfusion device of the second embodiment is described with reference to flow charts of FIGS. 13 to 17. When the power source switch 1 has been turned on at step F1, the CPU 30 clears the RAM 32 at step F2. Then, at step F3, it is judged whether or not input of the numerical keys 5 (or the clear key 6 as required) has been performed. In the case of "YES" at step F3, it is judged that transfusion quantity and transfusion rate have been inputted, so that the program flow proceeds to step F4. Thus, at step F4, data of transfusion quantity and transfusion rate are stored in the RAM 32. After step F4 or in the case of "NO" at step F3, the program flow proceeds to step F5 at which it is judged by the bar code reader 40 whether or not the bar code has been inputted. In the case of "NO" at step F5, the program flow proceeds to step F6 at which it is judged whether or not the transfusion starting key 4c has been depressed. In the case of "NO" at step F6, the program flow returns to step F3 at which input operation is requested. On the other hand, in the case of "YES" at step F6, the program flow proceeds to step F11.

Meanwhile, in the case of "YES" at step F5, the program flow proceeds to step F7 at which it is judged through confirmation of the drug container code ID whether or not the bar code identified at step F5 is a drug container code attached to the drug container. In the case of "YES" at step F7, the program flow proceeds to step F8 at which the drug code, the maximum transfusion quantity, the maximum transfusion rate, the maximum transfusion period, the minimum transfusion quantity, the minimum transfusion rate, the minimum transfusion period and the container capacity contained in the drug container code are stored in the RAM 32 and are displayed in the programming display 3. FIG. 18 shows one example of a display screen of the programming display 3. In FIG. 18, the uppermost row "Code= 123456" indicates the drug code, the second row "RATE= 100–1500" indicates a minimum transfusion rate of 100 and a maximum transfusion rate of 1,500, the third row "VTBI= 0–600" indicates a minimum transfusion quantity of 0 and a maximum transfusion quantity of 600, the fourth row "TIME= 00:00–99:99" indicates a minimum transfusion period of 0 and a maximum transfusion period of 99 and the lowermost row "NET=650" indicates a container capacity of 650. After step F8, the program flow returns to step F3 such that input operation is repeated.

In the case of "NO" at step 7, the program flow proceeds to step F9 at which it is judged through confirmation of the prescription code ID whether or not the bar code identified at step F5 is the prescription code attached to the prescription. In the case of "NO" at step F9, an error display is made in the alarm/warning display 2 at step S10 and then, the program flow returns to step F3 such that input operation is repeated. On the contrary, in the case of "YES" at step F9, the program flow proceeds to step F17 (FIG. 15) to be described later.

Figure 14:
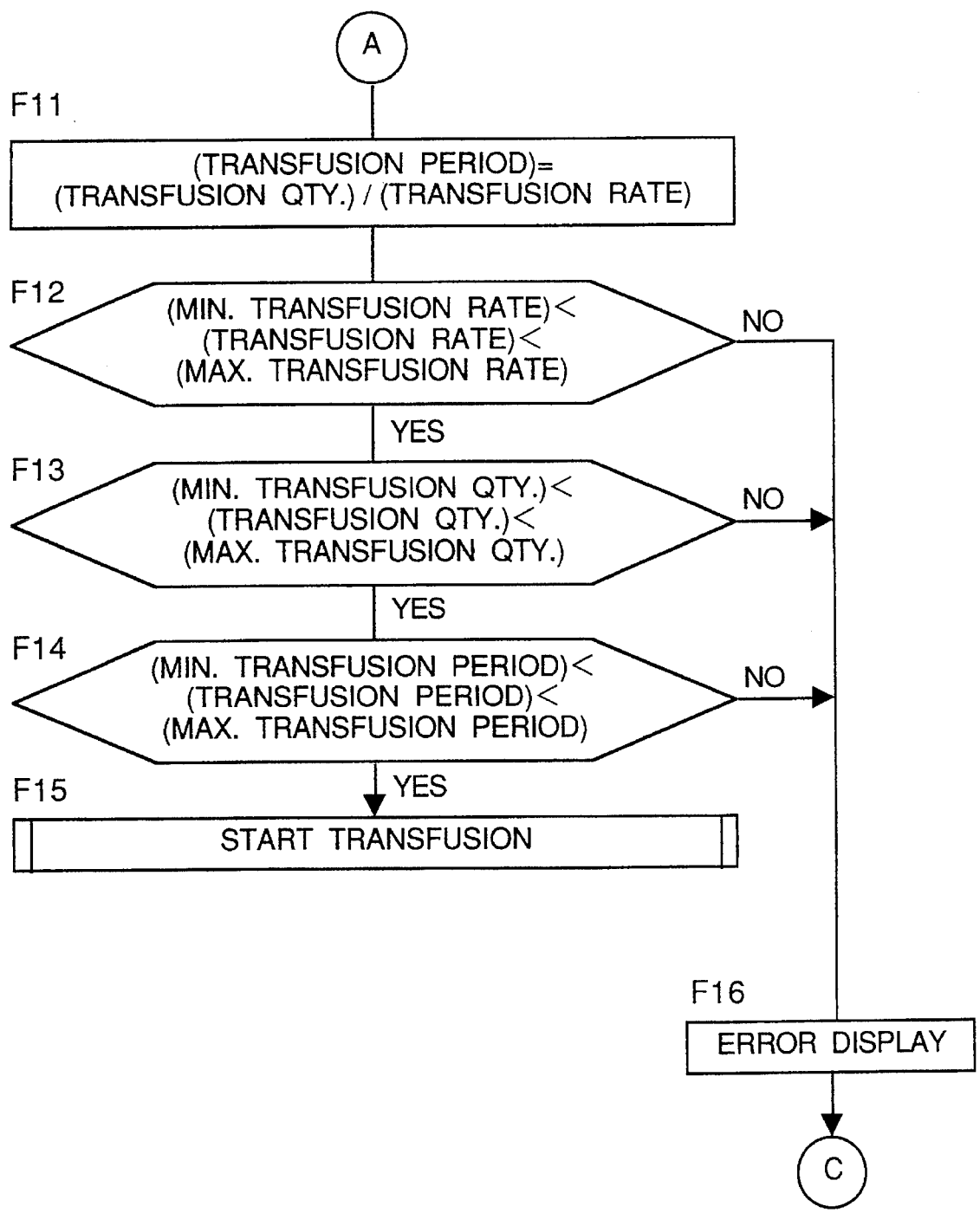

It is supposed here that the program flow has proceeds from step F3 to step F11 shown in FIG. 14 via steps F4, F5, F7, F8, F3, F5 and F6. At step F11, transfusion period is calculated on the basis of the equation [transfusion period= transfusion quantity/transfusion rate] from the transfusion quantity and the transfusion rate set at step F4. Subsequently, at step F12, it is judged whether or not the transfusion rate set at step F4 falls between the minimum transfusion rate and the maximum transfusion rate recorded at step F8 in the drug container code. In the case of "NO" at step 12, an error display is made in the programming display 3 at step F16 and then, the program flow returns to step F3 such that input operation is repeated. On the other hand, in the case of "YES" at step F12, the program flow proceeds to step F13 at which it is judged whether or not the transfusion quantity set at step F4 falls between the minimum transfusion quantity and the maximum transfusion quantity recorded at step F8 in the drug container code. In the case of "NO" at step F13, an error display is made in the programming display 3 at step F16 and then, the program flow returns to step F3 such that input operation is repeated. On the contrary, in the case of "YES" at step F13, the program flow proceeds to step F14 at which it is judged whether or not the transfusion period calculated at step F11 falls between the minimum transfusion period and the maximum transfusion period recorded at step F8. In the case of "NO" at step 14, an error display is made in the programming display 3 at step F16 and then, the program flow proceeds to step F3 such that input operation is repeated. On the other hand, in the case of "YES" at step F14, it is judged that conditions for transfusion have been satisfied, so that the program flow proceeds to step F15 at which the stepping motor 36 is driven by controlling the motor drive circuit 35 so as to start transfusion.

As described above, in the case of "NO" at step F12, F13 or F14, an error display is made at step F16 and then, the program flow returns to step F3 such that input operation is repeated. Accordingly, it is possible to positively prevent an erroneous human error of input.

Figure 13:
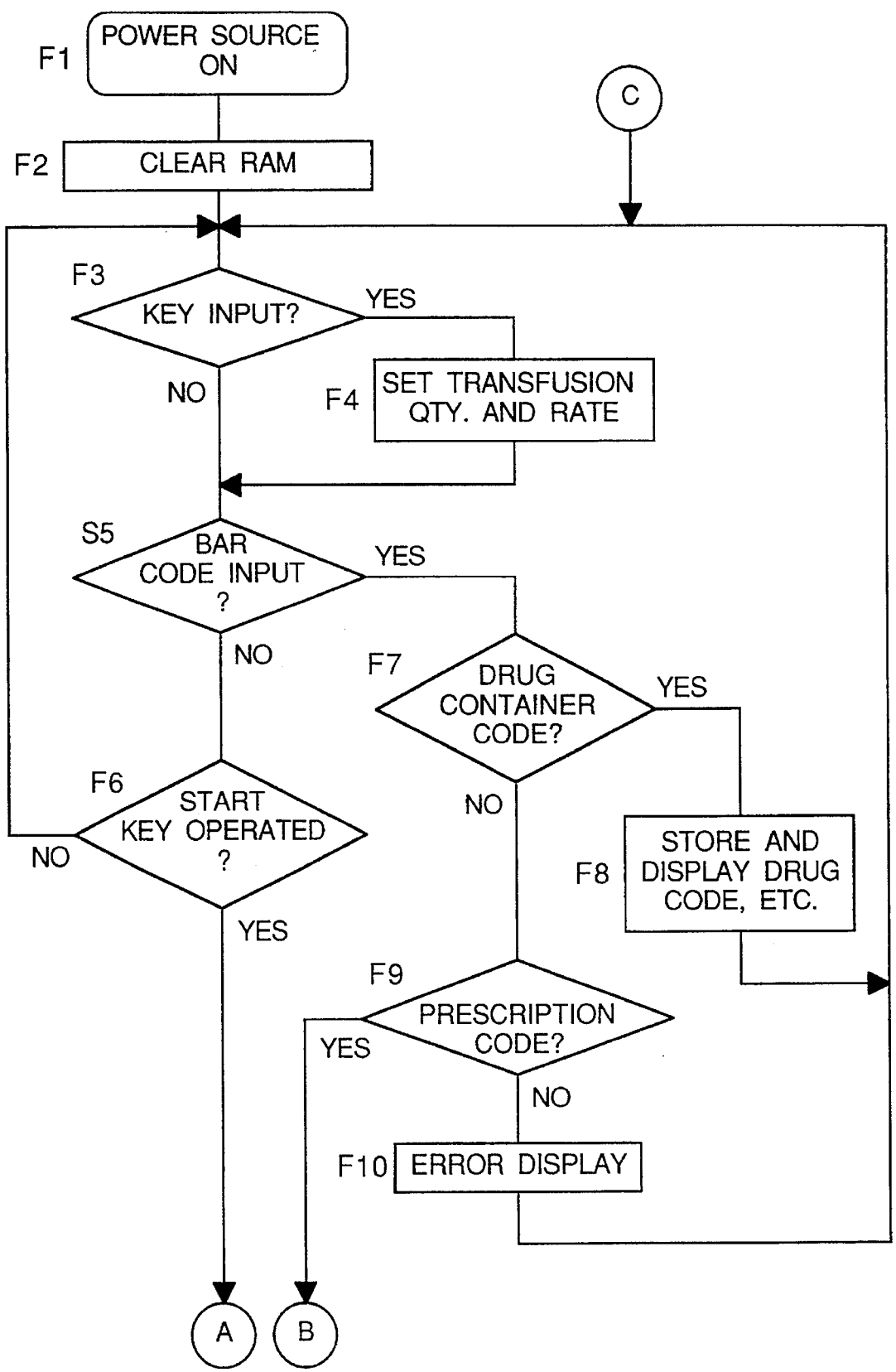
FIGS. 13 to 17 are flow charts explanatory of operation of the transfusion device of FIG. 12.
Figure 15:
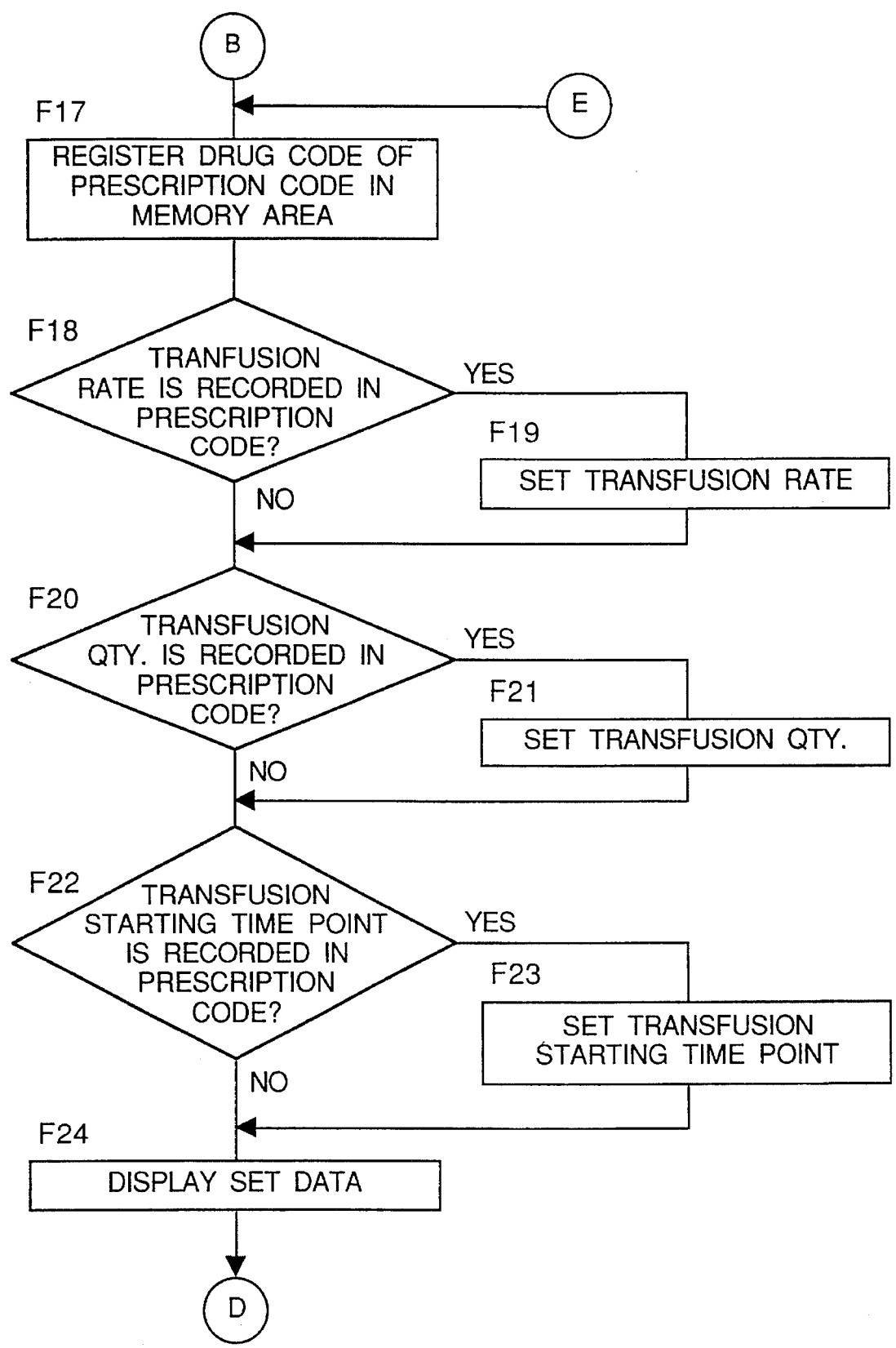
Figure 16:
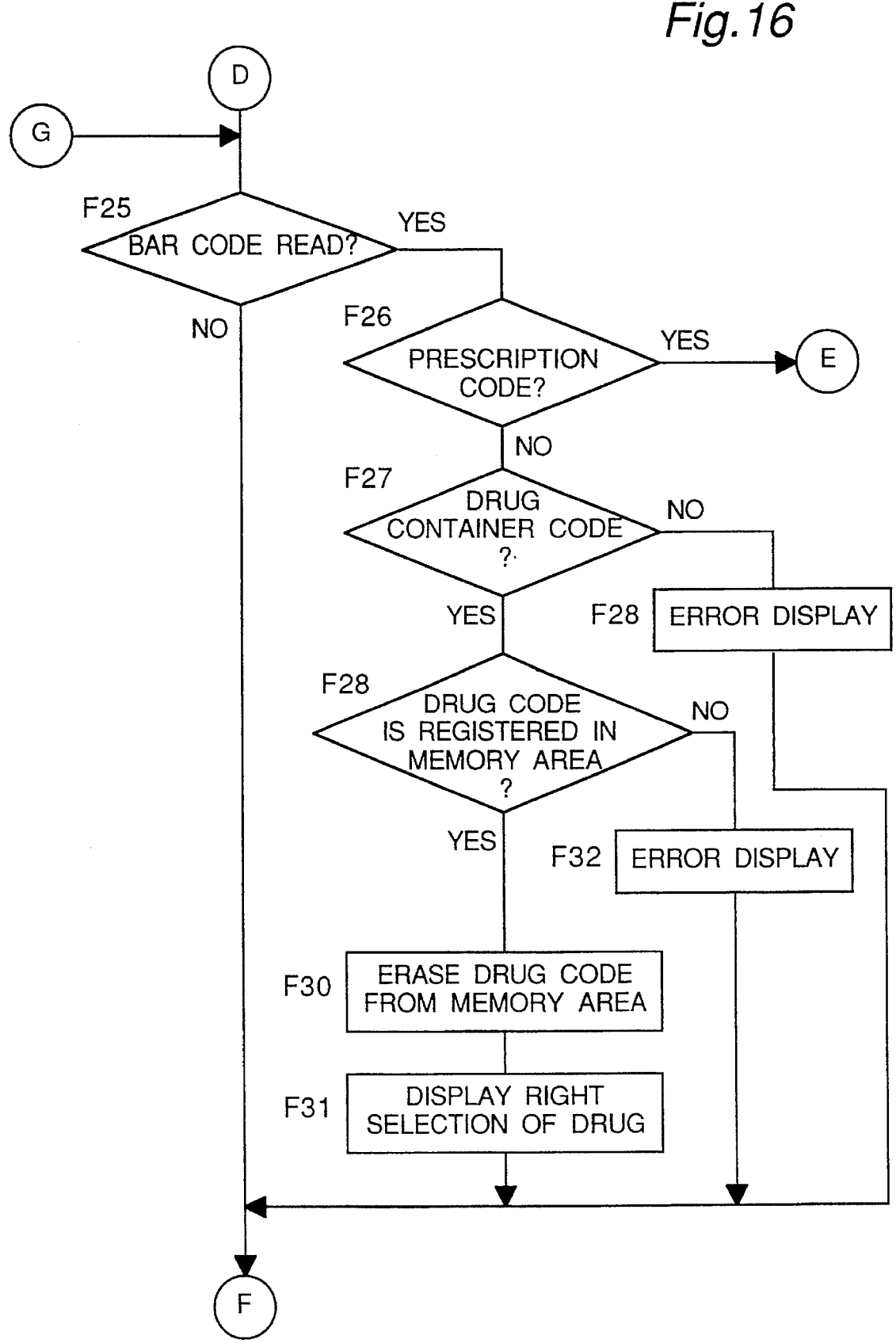

If the read bar code is not the drug container code but the prescription code, the program flow proceeds from step F9 of FIG. 13 to step F17 of FIG. 15. At step F17, the drug code of the prescription code is registered in an memory area M in the RAM 32. Then, at step F18, it is judged whether or not the transfusion rate is recorded in the prescription code. In the case of "YES" at step F18, the transfusion rate is set in the RAM 32 at step 19 followed by step F20. On the other hand, in the case of "NO" at step F18, the program flow proceeds directly to step F20. At step F20, it is judged whether or not the transfusion quantity is recorded in the prescription code. In the case of "YES" at step F20, the transfusion quantity is set in the RAM 32 at step F21 followed by step F22. On the contrary, in the case of "NO" at step F20, the program flow proceeds directly to step F22. At step F22, it is judged whether or not the transfusion starting time point is recorded in the prescription code. In the case of "YES" at step F22, the transfusion starting time point is set in the RAM 32 at step F23 followed by step F24. On the other hand, in the case of "NO" at step F22, the program flow proceeds directly to step F24. At step F24, the data set at steps F17 to F23 are displayed in the programming display 3.

FIG. 19 shows one example of a display screen of the programming display 3. The transfusion rate is displayed as "125" and the transfusion quantity is displayed as "500". Since two kinds of drugs are registered, a display of "AB" is made. When the prescription code has been read twice or more at step F26 of FIG. 16 to be described later so as to perform transfusion continuously, the programming display 3 has a display state shown in FIG. 20. In FIG. 20, numerals "1", "2" and "3" below "N" at the left end of the second, third and fourth rows indicate that transfusion is performed at transfusion rates of 125, 60 and 125, respectively. Meanwhile, overlap of the drug notations "A" and "B" indicates that the same drug is used. At step F25 of FIG. 25, it is judged whether or not the bar code has been read by the bar code reader 40. In the case of "YES" at step F25, the program flow proceeds to step F26. On the contrary, in the case of "NO" at step F25, the program flow proceeds to step F33 of FIG. 17. At step F26, it is judged through confirmation of the prescription code ID whether or not the bar code identified at step F25 is the prescription code attached to the prescription. In the case of "YES" at step F26, the program flow returns to step F17 of FIG. 15. In this case, processings of steps F17 and so on are performed such that the prescription code read this time is contents for continuous transfusion subsequent to the prescription code read previously. On the other hand, in the case of "NO" at step F26, the program flow proceeds to step F27. At step F27, it is judged through confirmation of the drug container code ID whether or not the bar code identified at step F25 is the drug container code attached to the drug container. In the case of "NO" at step F27, the program flow proceeds to step F28. In this case, since the identified bar code is neither the drug container code nor the prescription code, an error display is made in the alarm/warning display 2 as an error of the bar code at step F28 followed by step F33 of FIG. 17. On the other hand, in the case of "YES" at step F27, the program flow proceeds to step F29. At step F29, it is judged whether or not the drug code of the drug container code identified at step F27 is registered in the memory area M. In the case of "NO" at step F29, since an erroneous drug is used, an error display is made in the alarm/warning display 2 at step F32 followed by step F33. On the contrary, in the case of "YES" at step F29, since use of the drug is considered as being right, the program flow proceeds to step F30 at which the drug code is erased from the memory area M. Subsequently, right selection of the drug is displayed in the programming display 3 at step F31 followed by step F33.

FIGS. 21 and 22 show examples of a display screen of the programming display 3 at step F31. FIG. 21 corresponds to FIG. 19, while FIG. 22 corresponds to FIG. 20. By displaying the selected drug through black-and-white inversion, right selection of the drug is indicated.

Figure 17:
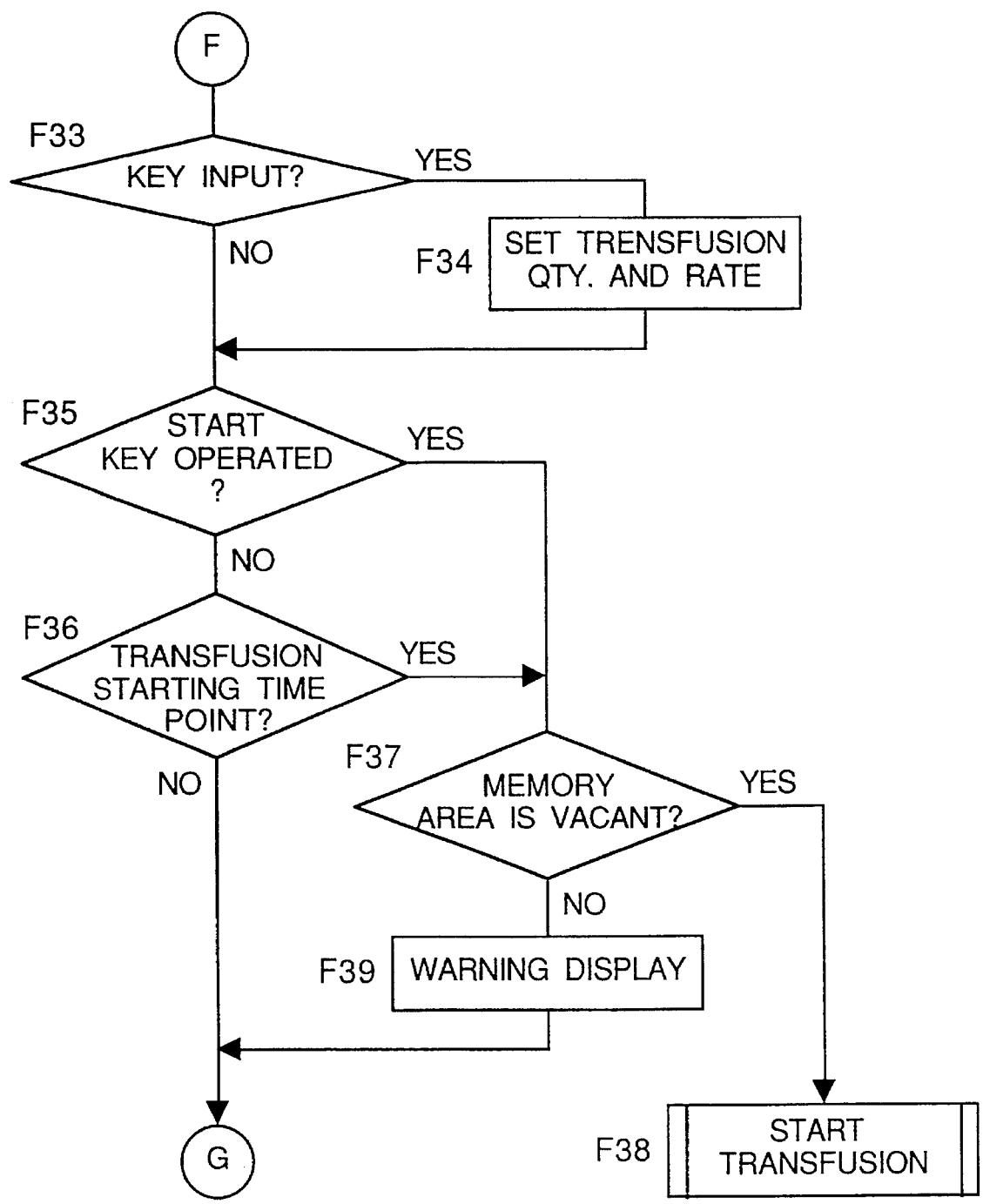

At step F33 of FIG. 17, it is judged whether or not input of the numerical keys 5 has been performed. In the case of "YES" at step F33, since it is considered that the transfusion quantity and the transfusion rate have been inputted, the program flow proceeds to step F34 at which the inputted transfusion quantity and transfusion rate are stored in the RAM 32. Then, the program flow proceeds to step F35. On the other hand, in the case of "NO" at step F33, the program flow proceeds directly to step F35. At step F35, it is judged whether or not the transfusion starting key 4c has been depressed. In the case of "NO" at step F35, the program flow proceeds to step F36. On the contrary, in the case of "YES" at step F35, the program flow proceeds to step F37. At step F36, it is judged whether or not time has reached the transfusion starting time point. In the case of "NO" at step F36, the program flow returns to step F25 such that steps F25 to F36 are repeated subsequently. On the other hand, in the case of "YES" at step F36, the program flow proceeds to step F37.

At step F37, it is judged whether or not the memory area M is vacant as a result of erasure (step F30) of all the drug codes registered in the memory area M at step F17. Namely, it is judged at step F37 whether or not selection of all the drugs is right. In the case of "NO" at step F37, it is clear that at least one drug has been selected erroneously. Thus, a warning display is made in the alarm/warning display 2 at step F39 and then, the program flow proceeds to step F25. On the contrary, in the case of "YES" at step F37, it is apparent that all the selected drugs are right. Thus, at step F38, the stepping motor 36 is driven by controlling the motor drive circuit 35 such that transfusion is started by the transfusion pump mechanism 17.

In the second embodiment, the bar code reader is employed as a data reader. However, in case due to increase of information content of codes, the bar code reader is not suitable for use in view of information content of the bar code, the codes having increased information content may be stored in a magnetic recording medium or an IC card in place of the bar code reader.

Meanwhile, when the code is not described on the drug container, the drug container code should be recorded on the drug container when the drug is supplied at a drugstore or the like. Furthermore, when a prescription is issued, a prescription code should be recorded.

In the first transfusion device of the present invention, size of air bubbles to be detected can be selected and permissible quantity of air bubbles mixed into the unit volume of the transfusion solution is determined as the bubble criterion on the basis of the selected size of air bubbles and the transfusion rate such that pressurization feed of the transfusion solution is stopped automatically when the actual measurement of the ultrasonic type bubble sensor has exceeded the bubble criterion. Therefore, detection accuracy of quantity of air bubbles mixed into the transfusion solution can be raised as that per unit volume of the transfusion solution and thus, safety of the transfusion device can be improved.

In the second transfusion device of the present invention, size of air bubbles to be detected can be selected and permissible quantity of air bubbles mixed into the transfusion solution during the unit time period is determined as the bubble criterion on the basis of the selected size of air bubbles and the transfusion rate such that pressurization feed of the transfusion solution is stopped automatically when the actual measurement of the ultrasonic type bubble sensor has exceeded the bubble criterion. Therefore, detection accuracy of quantity of air bubbles mixed into the transfusion solution can be raised as that per unit time period, so that safety of the transfusion device can be improved in the same manner as the first transfusion device.

In the third transfusion device of the present invention, since the data on the transfusion factors such as the transfusion quantity, the transfusion rate, the transfusion period, etc. can be automatically set by the data reader, labor saving can be achieved.

Meanwhile, in the fourth transfusion device of the present invention, when the transfusion factors such as the transfusion quantity, the transfusion rate, the transfusion period, etc. have been inputted, the threshold values of the transfusion factors are read by the data reader such that a warning is issued automatically when the inputted transfusion factors deviate from the threshold values. Accordingly, erroneous input of the transfusion factors can be prevented.

Furthermore, in the fifth transfusion device of the present invention, the drug code recorded on the drug container and the drug code recorded on the prescription or the like are read by the data reader so as to be compared with each other such that a warning is issued when the drug codes do not coincide with each other. Therefore, such a risk can be avoided beforehand that an erroneous drug is used.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A transfusion device in which a transfusion tube is squeezed by a transfusion pump mechanism so as to feed transfusion solution in the transfusion tube through pressurization, comprising:

first means operatively connected to the transfusion device for setting sizes of air bubbles to be detected in the transfusion solution, the first means including a bubble sensor formed by an ultrasonic transmitter and an ultrasonic receiver; the ultrasonic transmitter and the ultrasonic receiver being located on an outer periphery of the transfusion tube so as to be opposed to each other through the transfusion tube;

said first means also for setting a transfusion rate and a transfusion quantity of the transfusion solution;

a second means responsive to said first means for calculating a pressurization feed rate of the transfusion solution on the basis of the transfusion rate and a cross-sectional area of the transfusion tube;

third means responsive to said first and second means for calculating a permissible quantity of the air bubbles mixed into a unit volume of the transfusion solution on the basis of the size of the air bubbles and the transfusion rate;

fourth means responsive to said third means for calculating an integrated value of the air bubbles per unit volume of the transfusion solution on the basis of the pressurization feed rate of the transfusion solution and output level of the bubble sensor;

fifth means responsive to said fourth means for judging whether or not the integrated value of the air bubbles per unit volume of the transfusion solution exceeds the permissible quantity of the air bubbles mixed into the unit volume of the transfusion solution; and sixth means responsive to said fifth means for stopping, when the fifth means has judged that the integrated value of the air bubbles per unit volume of the transfusion solution exceeds the permissible quantity of the air bubbles mixed into the unit volume of the transfusion solution, the transfusion pump mechanism.

2. A transfusion device in which a transfusion tube is squeezed by a transfusion pump mechanism so as to feed transfusion solution in the transfusion tube through pressurization, comprising:

first means operatively connected to the transfusion device for setting sizes of air bubbles to be detected in the transfusion solution, the first means including a bubble sensor formed by an ultrasonic transmitter and an ultrasonic receiver; the ultrasonic transmitter and the ultrasonic receiver being located on an outer periphery of the transfusion tube so as to be opposed to each other through the transfusion tube;

said first means also for setting a transfusion rate and a transfusion quantity of the transfusion solution;

second means responsive to said first means for calculating a pressurization feed rate of the transfusion solution on the basis of the transfusion rate and a cross-sectional area of the transfusion tube;

third means responsive to said first and second means for calculating a permissible quantity of the air bubbles mixed into the transfusion solution during a unit time period of the basis of the size of the air bubbles and the transfusion rate;

fourth means responsive to the third means for calculating an integrated value of the air bubbles at an interval of the unit time period on the basis of the pressurization feed rate of the transfusion solution and output level of the bubble sensor;

fifth means responsive to said fourth means for judging whether or not the integrated value of the air bubbles at the interval of the unit time period exceeds the permissible quantity of the air bubbles mixed into the transfusion solution during the unit time period; and sixth means responsive to said fifth means for stopping, when the fifth means has judged that the integrated value of the air bubbles at the interval of the unit time period exceeds the permissible quantity of the air bubbles mixed into the transfusion solution during the unit time period, the transfusion pump mechanism.

3. The transfusion device according to claim 1, wherein the first means include hand operable keys.

4. The transfusion device according to claim 2, wherein the first means include hand operable keys.

* * * * *